US007029812B2

(12) United States Patent
Tokarski et al.

(10) Patent No.: US 7,029,812 B2
(45) **Date of Patent: *Apr. 18, 2006**

(54) ORGANOPHOTORECEPTOR WITH CHARGE TRANSPORT COMPOUND HAVING AN EPOXY GROUP

(75) Inventors: Zbigniew Tokarski, Woodbury, MN (US); Nusrallah Jubran, St. Paul, MN (US); Kam W. Law, Woodbury, MN (US); Vytautas Getautis, Kaunas (LT); Jonas V. Sidaravicius, Vilnius (LT); Maryte Daskeviciene, Jonava (LT); Vygintas Jankauskas, Vilnius (LT); Edmundas Montrimas, Vilnius (LT); Valentas Gaidelis, Vilnius (LT); Albina Stanisauskaite, Kaunas (LT)

(73) Assignee: Samsung Electronics Co., Ltd., Suwon (KR)

( * ) Notice: Subject to any disclaimer, the term of this patent is extended or adjusted under 35 U.S.C. 154(b) by 139 days.

This patent is subject to a terminal disclaimer.

(21) Appl. No.: 10/634,164

(22) Filed: Aug. 5, 2003

(65) Prior Publication Data

US 2004/0081903 A1 Apr. 29, 2004

Related U.S. Application Data

(60) Provisional application No. 60/421,179, filed on Oct. 25, 2002, provisional application No. 60/421,228, filed on Oct. 25, 2002, provisional application No. 60/421,174, filed on Oct. 25, 2002.

(51) Int. Cl.
*G03G 5/04* (2006.01)
*C07D 303/36* (2006.01)

(52) U.S. Cl. ........................... 430/75; 430/79; 430/96; 430/124; 549/551

(58) Field of Classification Search ................. 430/75, 430/79, 96, 124; 549/551
See application file for complete search history.

(56) References Cited

U.S. PATENT DOCUMENTS

| | | | | |
|---|---|---|---|---|
| 4,297,426 | A | 10/1981 | Sakai et al. | |
| 4,476,137 | A | 10/1984 | Haviv et al. | |
| 4,786,571 | A | 11/1988 | Ueda | |
| 4,957,838 | A | 9/1990 | Aruga et al. | |
| 5,128,227 | A | 7/1992 | Monbaliu et al. | |
| 5,187,036 | A * | 2/1993 | Matsui et al. | 430/58.4 |
| 5,274,116 | A | 12/1993 | Martin et al. | |
| 5,932,384 | A | 8/1999 | Mitsumori et al. | |
| 6,001,522 | A | 12/1999 | Woo et al. | |
| 6,020,096 | A | 2/2000 | Fuller et al. | |
| 6,030,734 | A | 2/2000 | Mitsumori | |
| 6,066,426 | A | 5/2000 | Mott et al. | |
| 6,099,996 | A | 8/2000 | Yanus et al. | |
| 6,140,004 | A | 10/2000 | Mott et al. | |
| 6,214,503 | B1 | 4/2001 | Gaidelis et al. | |
| 6,340,548 | B1 * | 1/2002 | Jubran et al. | 430/58.45 |
| 2003/0104294 | A1 | 6/2003 | Law et al. | |
| 2003/0113132 | A1 | 6/2003 | Law et al. | |
| 2003/0113643 | A1 | 6/2003 | Law et al. | |
| 2003/0113644 | A1 | 6/2003 | Law et al. | |
| 2003/0129513 | A1 | 7/2003 | Jubran et al. | |
| 2003/0138712 | A1 | 7/2003 | Law et al. | |
| 2003/0198880 | A1 | 10/2003 | Law et al. | |

FOREIGN PATENT DOCUMENTS

| | | |
|---|---|---|
| DE | 816923 | 12/1955 |
| EP | 1420303 | 5/2004 |
| GB | 1047525 | 9/1966 |
| JP | 2001-166519 | 6/2001 |
| JP | 2001166519 | 6/2001 |

OTHER PUBLICATIONS

Frank R. Atherton and Robert W. Lambert, *Synthesis of 3(S)-Acylamino-1-[(Phenyl)(1H-Tetrazol-5-YL)Amino]-2-Azetidinones*, Symposia-in-Part No. 10: Recent Aspects of the Chemistry of E-Lactams, 1983, vol. 39, No. 15., pp. 2599-2608.

(Continued)

*Primary Examiner*—John L Goodrow
(74) *Attorney, Agent, or Firm*—Patterson, Thuente, Skaar & Christensen, P.A.

(57) ABSTRACT

This invention relates to a novel organophotoreceptor that comprises an electrically conductive substrate and photoconductive element on the electrically conductive substrate, the photoconductive element having a) a novel charge transport compound having the formula

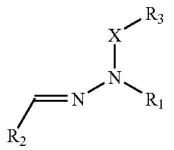

where X is a divalent hydrocarbon group of 1 to 30 carbon atoms, or a divalent hydrocarbon group of 1 to 30 carbon atoms where there is at least one substitution of a carbon atom by a heteroatom provided that no two heteroatoms may be adjacent within the backbone of an aliphatic divalent hydrocarbon radical, $R_1$ is an aryl group or a heterocyclic group, $R_2$ is a (N,N-disubstituted)arylamine group, and $R_3$ is an epoxy group; and (b) a charge generating compound.

The epoxy group can be reacted with a functional group within the polymer to form a polymeric charge transport compound either directly or through a crosslinking agent.

18 Claims, No Drawings

OTHER PUBLICATIONS

G. V. Boyd and S. R. Dando, *The Dimerisation of 5-Methylene-$\exists^2$-1,3,4-oxadiazolines*, Journal of The Chemical Society, 1971.

Yasuoki Murakami, Yuusaku Yokoyama, Chiyoko Sasakura, and Makiko Tamagawa, *An Efficient Synthesis of 1,1-Disubstituted Hydrazines*, Chemical & Pharmaceutical Bulletin, Feb. 1983, vol. 31, No. 2, pp. 423-428.

S.R. Jain, C.Oommen, S. Amanulla and K. Sridhara, *Novel Energetic N-N Bonded Polymeric Binders for Composite Propellants*, Macromolecules New Frontiers, publ. Allied Publishers Ltd.; 1998.

Paras N. Prasad and Jal K. Nigam, *Synthesis, Characterization and Binding Properties of Epoxy Resins Based on Carbonohydrazones and Thiocarbonohydrazones*, Frontiers of Polymer Research, Plenum Press, 1991.

Getautis et al., *Synthesis of Branched Hydrazones by Reaction of n-(2, 3- epoxypropyl)derivatives of Hydrazones with Benzenediols*, Chemistry of Heterocyclic Compounds, vol. 38, No. 7, Jul. 2002, pp. 778-782.

Stanisauskaite et al., *Synthesis of epoxypropyl derivatives of hydrazones*, Chemical Abstracts, p. 659, Column 1, dated 1996.

* cited by examiner

ORGANOPHOTORECEPTOR WITH CHARGE TRANSPORT COMPOUND HAVING AN EPOXY GROUP

CROSS REFERENCE TO RELATED APPLICATIONS

This application claims priority to copending U.S. Provisional Patent Applications Ser. No. 60/421,179 filed on Oct. 25, 2002 to Tokarski et al., entitled "Electrophotographic Organophotoreceptors With Novel Charge Transport Compounds Having An Epoxy Group,"incorporated herein by reference; Ser. No. 60/421,228 filed on Oct. 25, 2002 to Tokarski et al., entitled "Electrophotographic Organophotoreceptors With Novel Charge Transport Compounds Having An Epoxy Group," incorporated herein by reference; and Ser. No. 60/421,174 filed on Oct. 25, 2002 to Tokarski et al., entitled "Electrophotographic Organophotoreceptors With Novel Charge Transport Compounds Having An Epoxy Group," incorporated herein by reference.

FIELD OF THE INVENTION

This invention relates to organophotoreceptors suitable for use in electrophotography and, more specifically, to organophotoreceptors having a charge transport compound comprising at least an epoxy group, a hydrazone group and at least a (N,N-disubstituted)arylamine group. The epoxy group may or may not be covalently bonded with a polymer binder, directly or through a crosslinking compound.

BACKGROUND OF THE INVENTION

In electrophotography, an organophotoreceptor in the form of a plate, disk, sheet, belt, drum or the like having an electrically insulating photoconductive element on an electrically conductive substrate is imaged by first uniformly electrostatically charging the surface of the photoconductive layer, and then exposing the charged surface to a pattern of light. The light exposure selectively dissipates the charge in the illuminated areas where light strikes the surface, thereby forming a pattern of charged and uncharged areas, referred to as a latent image. A liquid or solid toner is then deposited in the vicinity of either the charged or uncharged areas depending on the properties of the toner to create a toned image on the surface of the photoconductive layer. The resulting toned image can be transferred to a suitable ultimate or intermediate receiving surface, such as paper, or the photoconductive layer can operate as an ultimate receptor for the image. The imaging process can be repeated many times to complete a single image, for example, by overlaying images of distinct color components or effect shadow images, such as overlaying images of distinct colors to form a full color final image, and/or to reproduce additional images.

Both single layer and multilayer photoconductive elements have been used. In single layer embodiments, a charge transport material and charge generating material are combined with a polymeric binder and then deposited on the electrically conductive substrate. In multilayer embodiments, the charge transport material and charge generating material are in the form of separate layers, each of which can optionally be combined with a polymeric binder, deposited on the electrically conductive substrate. Two arrangements are possible. In one arrangement (the "dual layer" arrangement), the charge generating layer is deposited on the electrically conductive substrate and the charge transport layer is deposited on top of the charge generating layer. In an alternate arrangement (the "inverted dual layer" arrangement), the order of the charge transport layer and charge generating layer is reversed.

In both the single and multilayer photoconductive elements, the purpose of the charge generating material is to generate charge carriers (i.e., holes and/or electrons) upon exposure to light. The purpose of the charge transport material is to accept at least one type of these charge carriers, generally holes, and transport them through the charge transport layer in order to facilitate discharge of a surface charge on the photoconductive element. The charge transport material can be a charge transport compound, an electron transport compound, or a combination of both. When a charge transport compound is used, the charge transport compound accepts the hole carriers and transports them through the layer in which the charge transport compound is located. When an electron transport compound is used, the electron transport compound accepts the electron carriers and transports them through the layer in which the electron transport compound is located.

SUMMARY OF THE INVENTION

This invention provides organophotoreceptors having good electrostatic properties such as high $V_{acc}$ and low $V_{dis}$.

In a first aspect, an organophotoreceptor comprises an electrically conductive substrate and a photoconductive element on the electrically conductive substrate, the photoconductive element comprising a) a charge transport compound having the formula:

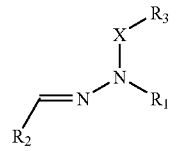

where X is a divalent hydrocarbon group of 1 to 30 carbon atoms, or a divalent hydrocarbon group of 1 to 30 carbon atoms where there is at least one substitution of a carbon atom by a heteroatom provided that no two heteroatoms may be adjacent within the backbone of an aliphatic divalent hydrocarbon radical, $R_1$ is an aryl group or a heterocyclic group, $R_2$ is a (N,N-disubstituted)arylamine group, and $R_3$ is an epoxy group; and (b) a charge generating compound.

The organophotoreceptor may be provided in the form of a plate, a flexible belt, a flexible disk, a sheet, a rigid drum, or a sheet around a rigid or compliant drum. In one embodiment, the organophotoreceptor includes: (a) a photoconductive element comprising the charge transport compound, the charge generating compound, the electron transport compound, and a polymeric binder; and (b) the electrically conductive substrate.

In a second aspect, the invention features an electrophotographic imaging apparatus that includes (a) a light imaging component; and (b) the above-described organophotoreceptor oriented to receive light from the light imaging component. The apparatus preferably further includes a toner dispenser, such as liquid toner dispenser. The method of electrophotographic imaging with photoreceptors containing these novel charge transport compounds is also described.

In a third aspect, the invention features an electrophotographic imaging process that includes (a) applying an electrical charge to a surface of the above-described organophotoreceptor; (b) imagewise exposing the surface of the organophotoreceptor to radiation to dissipate charge in selected areas and thereby form a pattern of at least relatively charged and uncharged areas on the surface; (c) contacting the surface with a toner, such as a liquid toner that includes a dispersion of colorant particles in an organic liquid, to create a toned image; and (d) transferring the toned image to a substrate.

In a fourth aspect, the invention features novel charge transport compounds having the general formula shown above.

In a fifth aspect, the invention features a polymeric charge transport compound prepared by the reaction of an epoxy group in a compound having the formula above reacted at the epoxy group with a reactive functionality in a binder directly or through a crosslinking agent. In some embodiments, the reactive functionality of the binder is selected from the group consisting of hydroxyl group, carboxyl group, amino group, and thiol group.

In a sixth aspect, the invention features organophotoreceptor comprising an electrically conductive substrate and a photoconductive element on the electrically conductive substrate, the photoconductive element comprising:

(a) a polymeric charge transport compound prepared by the reaction of an epoxy group in a compound having the formula above bonded at the epoxy functional group with a reactive functionality in a binder directly or through a crosslinking agent. In some embodiments, the reactive functionality is selected from the group consisting of hydroxyl group, carboxyl group, amino group, and thiol group; and (b) a charge generating compound.

The invention provides charge transport compounds for organophotoreceptors featuring a combination of good mechanical and electrostatic properties. These photoreceptors can be used successfully with toners, such as liquid toners, to produce high quality images. The high quality of the imaging system is maintained after repeated cycling.

Other features and advantages of the invention will be apparent from the following description of the preferred embodiments thereof, and from the claims.

DETAILED DESCRIPTION OF PREFERRED EMBODIMENTS

Charge transport compounds with desirable properties have a hydrazone group linked with at least one aryl group and an (N,N-disubstituted) arylamine group along with an epoxy group that can facilitate bonding of the charge transport compound with at least some polymer binders, either directly or through a linking group. These charge transport compounds have desirable properties as evidenced by their performance in organophotoreceptors for electrophotography. In particular, the charge transport compounds of this invention have high charge carrier mobilities and good compatibility with various binder materials, can be crosslinked in both the single and multilayer photoconductive elements, and possess excellent electrophotographic properties. The organophotoreceptors according to this invention generally have a high photosensitivity, a low residual potential, and a high stability with respect to cycle testing, crystallization, and organophotoreceptor bending and stretching. The organophotoreceptors are particularly useful in laser printers and the like as well as photocopiers, scanners and other electronic devices based on electrophotography. The use of these charge transport compounds is described in more detail below in the context of laser printer use, although their application in other devices operating by electrophotography can be generalized from the discussion below.

To produce high quality images, particularly after multiple cycles, it is desirable for the charge transport compounds to form a homogeneous solution with the polymeric binder and remain approximately homogeneously distributed through the organophotoreceptor material during the cycling of the material. In addition, it is desirable to increase the amount of charge that the charge transport material, such as a charge transport compound, can accept (indicated by a parameter known as the acceptance voltage or "$V_{acc}$"), and to reduce retention of that charge upon discharge (indicated by a parameter known as the discharge voltage or "$V_{dis}$").

There are many charge transport compounds available for electrophotography. Examples of charge transport compounds include, for example, pyrazoline derivatives, fluorene derivatives, oxadiazole derivatives, stilbene derivatives, enamine derivatives, hydrazone derivatives, carbazole hydrazone derivatives, triaryl amines, polyvinyl carbazole, polyvinyl pyrene, polyacenaphthylene, or multi-hydrazone compounds comprising at least two hydrazone groups and at least two groups selected from the group consisting of p-(N,N-disubstituted) arylamine such as triphenylamine and heterocycles such as carbazole, julolidine, phenothiazine, phenazine, phenoxazine, phenoxathin, thiazole, oxazole, isoxazole, dibenzo(1,4)dioxine, thianthrene, imidazole, benzothiazole, benzotriazole, benzoxazole, benzimidazole, quinoline, isoquinoline, quinoxaline, indole, indazole, pyrrole, purine, pyridine, pyridazine, pyrimidine, pyrazine, triazole, oxadiazole, tetrazole, thiadiazole, benzisoxazole, benzisothiazole, dibenzofuran, dibenzothiophene, thiophene, thianaphthene, quinazoline, or cinnoline. However, there is a need for other charge transport compounds to meet the various requirements of particular electrophotography applications.

In electrophotography applications, a charge generating compound within an organophotoreceptor absorbs light to form electron-hole pairs. These electron-hole pairs can be transported over an appropriate time frame under a large electric field to discharge locally a surface charge that is generating the field. The discharge of the field at a particular location results in a surface charge pattern that essentially matches the pattern drawn with the light. This charge pattern then can be used to guide toner deposition. The charge transport compounds described herein are especially effective at transporting charge, and in particular holes from the electron-hole pairs formed by the charge generating compound. In some embodiments, a specific electron transport compound can also be used along with the charge transport compound.

The layer or layers of materials containing the charge generating compound and the charge transport compounds are within an organophotoreceptor. To print a two dimensional image using the organophotoreceptor, the organophotoreceptor has a two dimensional surface for forming at least a portion of the image. The imaging process then continues by cycling the organophotoreceptor to complete the formation of the entire image and/or for the processing of subsequent images.

The organophotoreceptor may be provided in the form of a plate, a flexible belt, a disk, a rigid drum, a sheet around a rigid or compliant drum, or the like. The charge transport compound can be in the same layer as the charge generating compound and/or in a different layer from the charge generating compound. Additional layers can be used also, as described further below.

In some embodiments, the organophotoreceptor material comprises, for example: (a) a charge transport layer comprising the charge transport compound and a polymeric binder; (b) a charge generating layer comprising the charge generating compound and a polymeric binder; and (c) the electrically conductive substrate. The charge transport layer may be intermediate between the charge generating layer and the electrically conductive substrate. Alternatively, the charge generating layer may be intermediate between the charge transport layer and the electrically conductive substrate. In further embodiments, the organophotoreceptor material has a single layer with both a charge transport compound and a charge generating compound within a polymeric binder.

The organophotoreceptors can be incorporated into an electrophotographic imaging apparatus, such as laser printers. In these devices, an image is formed from physical embodiments and converted to a light image that is scanned onto the organophotoreceptor to form a surface latent image. The surface latent image can be used to attract toner onto the surface of the organophotoreceptor, in which the toner image is the same or the negative of the light image projected onto the organophotoreceptor. The toner can be a liquid toner or a dry toner. The toner is subsequently transferred, from the surface of the organophotoreceptor, to a receiving surface, such as a sheet of paper. After the transfer of the toner, the entire surface is discharged, and the material is ready to cycle again. The imaging apparatus can further comprise, for example, a plurality of support rollers for transporting a paper receiving medium and/or for movement of the photoreceptor, a light imaging component with suitable optics to form the light image, a light source, such as a laser, a toner source and delivery system and an appropriate control system.

An electrophotographic imaging process generally can comprise (a) applying an electrical charge to a surface of the above-described organophotoreceptor; (b) imagewise exposing the surface of the organophotoreceptor to radiation to dissipate charge in selected areas and thereby form a pattern of charged and uncharged areas on the surface; (c) exposing the surface with a toner, such as a liquid toner that includes a dispersion of colorant particles in an organic liquid to create a toner image, to attract toner to the charged or discharged regions of the organophotoreceptor; and (d) transferring the toner image to a substrate.

This invention features an organophotoreceptor that comprises a charge transport compound having the formula

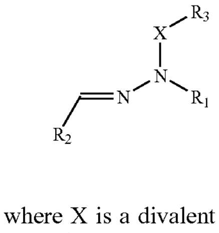

where X is a divalent hydrocarbon group of generally 1 to 30 carbon atoms, or a divalent hydrocarbon group of generally 1 to 30 carbon atoms where there is at least one substitution of a carbon atom by a heteroatom provided that no two heteroatoms may be adjacent within the backbone of an aliphatic divalent hydrocarbon radical, $R_1$ is an aryl group or a heterocyclic group, $R_2$ is a (N,N-disubstituted)arylamine group, such as a p-(N,N-disubstituted) aryl amine group (e.g., triphenylamine), carbazole or julolidine, and $R_3$ is an epoxy group. The divalent hydrocarbon radical X may be aliphatic, aromatic, or mixed aliphatic-aromatic. In some embodiments, $R_2$ may be divalent such that the $R_2$ group bridges between two hydrazone groups to form a bridged dihydrazone compound. When forming the organophotoreceptor, the epoxy group may or may not be reacted with a function group of the binder or a crosslinking agent that crosslinks the charge transport compound with the binder. A suitable crosslinking agent has suitable multiple functionality to react with the epoxy group and a functional group of the binder.

Substitution is liberally allowed on the chemical groups to affect various physical effects on the properties of the compounds, such as mobility, sensitivity, solubility, stability, and the like, as is known generally in the art. In the description of chemical substituents, there are certain practices common to the art that are reflected in the use of language. The term group indicates that the generically recited chemical entity (e.g., alkyl group, phenyl group, julolidine group, (N,N-disubstituted) arylamine group, etc.) may have any substituent thereon which is consistent with the bond structure of that group. For example, where the term 'alkyl group' is used, that term would not only include unsubstituted linear, branched and cyclic alkyls, such as methyl, ethyl, isopropyl, tert-butyl, cyclohexyl, dodecyl and the like, but also substituents such as hydroxyethyl, cyanobutyl, 1,2,3-trichloropropane, and the like. However, as is consistent with such nomenclature, no substitution would be included within the term that would alter the fundamental bond structure of the underlying group. For example, where a phenyl group is recited, substitution such as 1-hydroxyphenyl, 2,4-fluorophenyl, orthocyanophenyl, 1,3,5-trimethoxyphenyl and the like would be acceptable within the terminology, while substitution of 1,1,2,2,3,3-hexamethylphenyl would not be acceptable as that substitution would require the ring bond structure of the phenyl group to be altered to a non-aromatic form because of the substitution. Similarly, when referring to epoxy group, the compound or substituent cited includes any substitution that does not substantively alter the chemical nature of the epoxy ring in the formula. When referring p-(N,N-disubstituted) arylamine group, the two substituents attached to the nitrogen may be any group that will not substantively alter the chemical nature of the amine group. Where the term moiety is used, such as alkyl moiety or phenyl moiety, that terminology indicates that the chemical material is not substituted. Where the term alkyl moiety is used, that term represents only an unsubstituted alkyl hydrocarbon group, whether branched, straight chain, or cyclic.

Organophotoreceptors

The organophotoreceptor may be, for example, in the form of a plate, a sheet, a flexible belt, a disk, a rigid drum, or a sheet around a rigid or compliant drum, with flexible belts and rigid drums generally being used in commercial embodiments. The organophotoreceptor may comprise, for example, an electrically conductive substrate and on the electrically conductive substrate a photoconductive element in the form of one or more layers. The photoconductive element can comprise both a charge transport compound and a charge generating compound in a polymeric binder, which may or may not be in the same layer, as well as an electron transport compound in some embodiments. For example, in some embodiments with a single layer construction, the charge transport compound and the charge generating compound are in a single layer. In other embodiments, however, the photoconductive element comprises a bilayer construction featuring a charge generating layer and a separate charge transport layer. The charge generating layer may be located intermediate between the electrically conductive substrate and the charge transport layer. Alternatively, the photoconductive element may have a structure in which the charge transport layer is intermediate between the electrically conductive substrate and the charge generating layer.

The electrically conductive substrate may be flexible, for example in the form of a flexible web or a belt, or inflexible, for example in the form of a drum. A drum can have a hollow cylindrical structure that provides for attachment of the drum to a drive that rotates the drum during the imaging process. Typically, a flexible electrically conductive substrate comprises an electrically insulating substrate and a thin layer of electrically conductive material onto which the photoconductive material is applied.

The electrically insulating substrate may be paper or a film forming polymer such as polyester (e.g., polyethylene terephthalate or polyethylene naphthalate), polyimide, polysulfone, polypropylene, nylon, polyester, polycarbonate, polyvinyl resin, polyvinyl fluoride, polystyrene and the like. Specific examples of polymers for supporting substrates included, for example, polyethersulfone (STABAR™ S-100, available from ICI), polyvinyl fluoride (TEDLAR®, available from E.I. DuPont de Nemours & Company), polybisphenol-A polycarbonate (MAKROFOL™, available from Mobay Chemical Company) and amorphous polyethylene terephthalate (MELINAR™, available from ICI Americas, Inc.). The electrically conductive materials may be graphite, dispersed carbon black, iodide, conductive polymers such as polypyrroles and CALGON® conductive polymer 261 (commercially available from Calgon Corporation, Inc., Pittsburgh, Pa.), metals such as aluminum, titanium, chromium, brass, gold, copper, palladium, nickel, or stainless steel, or metal oxide such as tin oxide or indium oxide. In embodiments of particular interest, the electrically conductive material is aluminum. Generally, the photoconductor substrate has a thickness adequate to provide the required mechanical stability. For example, flexible web substrates generally have a thickness from about 0.01 to about 1 mm, while drum substrates generally have a thickness from about 0.5 mm to about 2 mm.

The charge generating compound is a material which is capable of absorbing light to generate charge carriers, such as a dye or pigment. Non-limiting examples of suitable charge generating compounds include, for example, metal-free phthalocyanines (e.g., ELA 8034 metal-free phthalocyanine available from H.W. Sands, Inc. or Sanyo Color Works, Ltd., CGM-X01), metal phthalocyanines such as titanium phthalocyanine, copper phthalocyanine, oxytitanium phthalocyanine (also referred to as titanyl oxyphthalocyanine, and including any crystalline phase or mixtures of crystalline phases that can act as a charge generating compound, e.g., ELA 7051 oxytitanyl phthalocyanine available from H.W. Sans, Inc.), hydroxygallium phthalocyanine, squarylium dyes and pigments, hydroxy-substituted squarylium pigments, perylimides, polynuclear quinones available from Allied Chemical Corporation under the tradename INDOFAST® Double Scarlet, INDOFAST® Violet Lake B, INDOFAST® Brilliant Scarlet and INDOFAST® Orange, quinacridones available from DuPont under the tradename MONASTRAL™ Red, MONASTRAL™ Violet and MONASTRAL™ Red Y, naphthalene 1,4,5,8-tetracarboxylic acid derived pigments including the perinones, tetrabenzoporphyrins and tetranaphthaloporphyrins, indigo-and thioindigo dyes, benzothioxanthene derivatives, perylene 3,4,9,10-tetracarboxylic acid derived pigments, polyazo-pigments including bisazo-, trisazo- and tetrakisazo-pigments, polymethine dyes, dyes containing quinazoline groups, tertiary amines, amorphous selenium, selenium alloys such as selenium-tellurium, selenium-tellurium-arsenic and selenium-arsenic, cadmium sulphoselenide, cadmium selenide, cadmium sulphide, and mixtures thereof. For some embodiments, the charge generating compound comprises oxytitanium phthalocyanine (e.g., any phase thereof), hydroxygallium phthalocyanine or a combination thereof.

The photoconductive layer of this invention may contain an electron transport compound. Generally, any electron transport compound known in the art can be used. Non-limiting examples of suitable electron transport compound include, for example, bromoaniline, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8-trinitrothioxanthone, 2,6,8-trinitro-4H-indeno[1,2-b]thiophene-4-one, and 1,3,7-trinitrodibenzo thiophene-5,5-dioxide, (2,3-diphenyl-1-indenylidene)malononitrile, 4H-thiopyran-1,1-dioxide and its derivatives such as 4-dicyanomethylene-2,6-diphenyl-4H-thiopyran-1,1-dioxide, 4-dicyanomethylene-2,6-di-m-tolyl-4H-thiopyran-1,1-dioxide, and unsymmetrically substituted 2,6-diaryl-4H-thiopyran-1,1-dioxide such as 4H-1,1-dioxo-2-(p-isopropylphenyl)-6-phenyl-4-(dicyanomethylidene)thiopyran and 4H-1,1-dioxo-2-(pisopropylphenyl)-6-(2-thienyl)-4-(dicyanomethylidene)thiopyran, derivatives of phospha-2,5-cyclohexadiene, alkoxycarbonyl-9-fluorenylidene)malononitrile derivatives such as (4-n-butoxycarbonyl-9-fluorenylidene)malononitrile, (4-phenethoxycarbonyl-9-fluorenyl-idene)malononitrile, (4-carbitoxy-9-fluorenylidene)malononitrile, and diethyl(4-n-butoxy carbonyl-2,7-dinitro-9-fluorenylidene)malonate, anthraquinodimethane derivatives such as 11,11,12,12-tetracyano-2-alkylanthraquinodimethane and 11,11-dicyano-12,12-bis(ethoxycarbonyl)anthraquinodimethane, anthrone derivatives such as 1-chloro-10-[bis(ethoxycarbonyl)methylene]anthrone, 1,8-dichloro-10-[bis(ethoxycarbonyl) methylene]anthrone, 1,8-dihydroxy-10-[bis(ethoxycarbonyl)methylene]anthrone, and 1-cyano-10-[bis(ethoxycarbonyl) methylene)anthrone, 7-nitro-2-aza-9-fluroenylidene-malononitrile, diphenoquinone derivatives, benzoquinone derivatives, naphtoquinone derivatives, quinine derivatives, tetracyanoethylenecyanoethylene, 2,4,8-trinitro thioxantone, dinitrobenzene derivatives, dinitroanthracene derivatives, dinitroacridine derivatives, nitroanthraquinone derivatives, dinitroanthraquinone derivatives, succinic anhydride, maleic anhydride, dibromo maleic anhydride, pyrene derivatives, carbazole derivatives, hydrazone derivatives, N,N-dialkylaniline derivatives, diphenylamine derivatives, triphenylamine derivatives, triphenylmethane derivatives, tetracyano quinoedimethane, 2,4,5,7-tetranitro-9-fluorenone, 2,4,7-trinitro-9-dicyanomethylene fluorenone, 2,4,5,7-tetranitroxanthone derivatives, and 2,4,8-trinitrothioxanthone derivatives. In some embodiments of interest, the electron transport compound comprises an (alkoxycarbonyl-9-fluorenylidene)malononitrile derivative, such as (4-n-butoxycarbonyl-9-fluorenylidene)malononitrile.

An electron transport compound and a UV light stabilizer can have a synergistic relationship for providing desired electron flow within the photoconductor. The presence of the UV light stabilizers alters the electron transport properties of the electron transport compounds to improve the electron transporting properties of the composite. UV light stabilizers can be ultraviolet light absorbers or ultraviolet light inhibitors that trap free radicals.

UV light absorbers can absorb ultraviolet radiation and dissipate it as heat. UV light inhibitors are thought to trap free radicals generated by the ultraviolet light and after trapping of the free radicals, subsequently to regenerate active stabilizer moieties with energy dissipation. In view of the synergistic relationship of the UV stabilizers with electron transport compounds, the particular advantages of the UV stabilizers may not be their UV stabilizing abilities, although the UV stabilizing ability may be further advantageous in reducing degradation of the organophotoreceptor over time. While not wanting to be limited by theory, the synergistic relationship contributed by the UV stabilizers may be related to the electronic properties of the compounds, which contribute to the UV stabilizing function, by further contributing to the establishment of electron conduction pathways in combination with the electron transport compounds. In particular, the organophotoreceptors with a combination of the electron transport compound and the UV stabilizer can demonstrate a more stable acceptance voltage $V_{acc}$ with cycling. The improved synergistic performance of organophotoreceptors with layers comprising both an electron transport compound and a UV stabilizer are described further in copending U.S. patent application Ser. No. 10/425,333 filed on Apr. 28, 2003 to Zhu, entitled "Organophotoreceptor With A Light Stabilizer," incorporated herein by reference.

Non-limiting examples of suitable light stabilizer include, for example, hindered trialkylamines such as TINUVIN™ 144 and TINUVIN™ 292 (from Ciba Specialty Chemicals, Terrytown, N.Y.), hindered alkoxydialkylamines such as TINUVIN™ 123 (from Ciba Specialty Chemicals), benzotriazoles such as TINUVIN™ 328, TINUVIN™ 900 and TINUVIN™ 928 (from Ciba Specialty Chemicals), benzophenones such as SANDUVOR™ 3041 (from Clariant Corp., Charlotte, N.C.), nickel compounds such as ARBESTAB™ (from Robinson Brothers Ltd, West Midlands, Great Britain), salicylates, cyanocinnamates, benzylidene malonates, benzoates, oxanilides such as SANDUVOR™ VSU (from Clariant Corp., Charlotte, N.C.), triazines such as CYAGARD™ UV-1164 (from Cytec Industries Inc., N.J.), polymeric sterically hindered amines such as LUCHEM™ (from Atochem North America, Buffalo, N.Y.). In some embodiments, the light stabilizer is selected from the group consisting of hindered trialkylamines having the following formula:

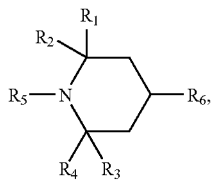

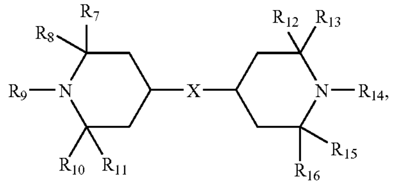

where $R_1$, $R_2$, $R_3$, $R_4$, $R_6$, $R_7$, $R_8$, $R_{10}$, $R_{11}$, $R_{12}$, $R_{13}$, $R_{14}$, $R_{15}$ are, independentlt, hydrogen, alkyl group, or ester, or ether group; and $R_5$, $R_9$, and $R_{14}$ are, independently, alkyl group; and X is a linking group selected from the group consisting of $—O—CO—(CH_2)_m—CO—O—$ where m is between 2 to 20.

Optionally, the photoconductive layer may comprise a crosslinking agent linking the charge transport compound and the binder. As is generally true for crosslinking agents in various contexts, the crosslinking agent comprises a plurality of functional groups or at least one functional group with the ability to exhibit multiple functionality. Specifically, a suitable crosslinking agent generally comprises at least one functional group that reacts with an epoxy group and at least one functional group reactive with a functional group of the polymer binder. Suitable functional groups for reacting with the epoxy group include, for example, a reactive active hydrogen functionality, such as hydroxyl, thiol, amino (primary amino or secondary amino), a carboxyl group or a combination thereof. In some embodiments, the reactive functional group for reacting with the polymer does not react significantly with the epoxy group. In general, a person of ordinary skill in the art can select the appropriate functional group of the crosslinking agent to react with the binder, or similarly, a person of ordinary skill in the art can select appropriate functional groups of the binder to react with the functional group of the crosslinking agent. Suitable functional groups of the crosslinking agent that do not react significantly with the epoxy group, at least under selected conditions, include, for example, epoxy groups, aldehydes and ketones. Suitable reactive binder functional groups for reacting with the aldehydes and ketones include, for example, amines.

In some embodiments, the crosslinking agent is a cyclic acid anhydride, which effectively is at least bifunctional. Non-limiting examples of suitable cyclic acid anhydrides include, for example, 1,8-naphthalene dicarboxylic acid anhydride, itaconic anhydride, glutaric anhydride and citraconic anhydride, fumaric anhydride, phthalic anhydride, isophthalic anhydride, and terephthalic anhydride with maleic anhydride and phthalic anhydride being of particular interest.

The binder generally is capable of dispersing or dissolving the charge transport compound (in the case of the charge transport layer or a single layer construction) and/or the charge generating compound (in the case of the charge generating layer or a single layer construction). Examples of suitable binders for both the charge generating layer and charge transport layer generally include, for example, polystyrene-co-butadiene, polystyrene-co-acrylonitrile, modified acrylic polymers, polyvinyl acetate, styrene-alkyd resins, soya-alkyl resins, polyvinylchloride, polyvinylidene chloride, polyacrylonitrile, polycarbonates, polyacrylic acid, polyacrylates, polymethacrylates, styrene polymers, polyvinyl butyral, alkyd resins, polyamides, polyurethanes, polyesters, polysulfones, polyethers, polyketones, phenoxy resins, epoxy resins, silicone resins, polysiloxanes, poly(hydroxyether) resins, polyhydroxystyrene resins, novolak, poly(phenylglycidyl ether)-co-dicyclopentadiene, copolymers of monomers used in the above-mentioned polymers, and combinations thereof. In some embodiments, the binder comprises a polymer with a reactive active hydrogen functionality, such as hydroxyl, thiol, amino (primary amino, secondary amino or tertiary amino), a carboxyl group or a combination thereof, that can react with the epoxy ring of the charge transport compounds of this invention or with a functional group of a crosslinking agent, such as a cyclic acid anhydride. In the organophotoreceptor, the functional group of the polymer can be bonded directly with the epoxy group or indirectly through a co-reactive crosslinking agent, for example, a cyclic acid anhydride group, to form the corresponding and predictable reaction product. Suitable binders with reactive functionality include, for example, polyvinyl butyral, such as BX-1 and BX-5 form Sekisui Chemical Co. Ltd., Japan.

Suitable optional additives for any one or more of the layers include, for example, antioxidants, coupling agents, dispersing agents, curing agents, surfactants, and combinations thereof.

The photoconductive element overall typically has a thickness from about 10 to about 45 microns. In the dual layer embodiments having a separate charge generating layer and a separate charge transport layer, charge generation layer generally has a thickness from about 0.5 to about 2 microns, and the charge transport layer has a thickness from about 5 to about 35 microns. In embodiments in which the charge transport compound and the charge generating compound are in the same layer, the layer with the charge generating compound and the charge transport composition generally has a thickness from about 7 to about 30 microns. In embodiments with a distinct electron transport layer, the electron transport layer has an average thickness from about 0.5 microns to about 10 microns and in further embodiments from about 1 micron to about 3 microns. In general, an electron transport overcoat layer can increase mechanical abrasion resistance, increases resistance to carrier liquid and atmospheric moisture, and decreases degradation of the photoreceptor by corona gases. A person of ordinary skill in the art will recognize that additional ranges of thickness within the explicit ranges above are contemplated and are within the present disclosure.

Generally, for the organophotoreceptors described herein, the charge generation compound is in an amount from about 0.5 to about 25 weight percent in further embodiments in an amount from about 1 to about 15 weight percent and in other embodiments in an amount from about 2 to about 10 weight percent, based on the weight of the photoconductive layer. The charge transport compound is in an amount from about 10 to about 80 weight percent, based on the weight of the photoconductive layer, in further embodiments in an amount from about 35 to about 60 weight percent, and in other embodiments from about 45 to about 55 weight percent, based on the weight of the photoconductive layer. The optional electron transport compound, when present, can be in an amount of at least about 2 weight percent, in other embodiments from about 2.5 to about 25 weight percent, based on the weight of the photoconductive layer, and in further embodiments in an amount from about 4 to about 20 weight percent, based on the weight of the photoconductive layer. The binder is in an amount from about 15 to about 80 weight percent, based on the weight of the photoconductive layer, and in further embodiments in an amount from about 20 to about 75 weight percent, based on the weight of the photoconductive layer. A person of ordinary skill in the art will recognize that additional ranges within the explicit ranges of compositions are contemplated and are within the present disclosure.

For the dual layer embodiments with a separate charge generating layer and a charge transport layer, the charge generation layer generally comprises a binder in an amount from about 10 to about 90 weight percent, in further embodiments from about 15 to about 80 weight percent and in some embodiments in an amount from about 20 to about 75 weight percent, based on the weight of the charge generation layer. The optional electron transport compound in the charge generating layer, if present, generally can be in an amount of at least about 2.5 weight percent, in further embodiments from about 4 to about 30 weight percent and in other embodiments in an amount from about 10 to about 25 weight percent, based on the weight of the charge generating layer. The charge transport layer generally comprises a binder in an amount from about 20 weight percent to about 70 weight percent and in further embodiments in an amount from about 30 weight percent to about 50 weight percent. A person of ordinary skill in the art will recognize that additional ranges of binder concentrations for the dual layer embodiments within the explicit ranges above are contemplated and are within the present disclosure.

For the embodiments with a single layer having a charge generating compound and a charge transport compound, the photoconductive layer generally comprises a binder, a charge transport compound and a charge generation compound. The charge generation compound can be in an amount from about 0.05 to about 25 weight percent and in further embodiment in an amount from about 2 to about 15 weight percent, based on the weight of the photoconductive layer. The charge transport compound can be in an amount from about 10 to about 80 weight percent, in other embodiments from about 25 to about 65 weight percent, in additional embodiments from about 30 to about 60 weight percent and in further embodiments in an amount from about 35 to about 55 weight percent, based on the weight of the photoconductive layer, with the remainder of the photoconductive layer comprising the binder, and optionally additives, such as any conventional additives. A single layer with a charge transport composition and a charge generating compound generally comprises a binder in an amount from about 10 weight percent to about 75 weight percent, in other embodiments from about 20 weight percent to about 60 weight percent, and in further embodiments from about 25 weight percent to about 50 weight percent. Optionally, the layer with the charge generating compound and the charge transport compound may comprise an electron transport compound. The optional electron transport compound, if present, generally can be in an amount of at least about 2.5 weight percent, in further embodiments from about 4 to about 30 weight percent and in other embodiments in an amount from about 10 to about 25 weight percent, based on the weight of the photoconductive layer. A person of ordinary skill in the art will recognize that additional composition ranges within the explicit compositions ranges for the layers above are contemplated and are within the present disclosure.

In general, any layer with an electron transport layer can advantageously further include a UV light stabilizer. In particular, the electron transport layer generally can comprise an electron transport compound, a binder and an optional UV light stabilizer. An overcoat layer comprising an electron transport compound is described further in copending U.S. patent application Ser. No. 10/396,536 to Zhu et al. entitled, "Organophotoreceptor With An Electron Transport Layer," incorporated herein by reference. For example, an electron transport compound as described above may be used in the release layer of the photoconductors described herein. The electron transport compound in an electron transport layer can be in an amount from about 10 to about 50 weight percent, and in other embodiments in an amount from about 20 to about 40 weight percent, based on the weight of the electron transport layer. A person of ordinary skill in the art will recognize that additional ranges of compositions within the explicit ranges are contemplated and are within the present disclosure.

The UV light stabilizer, if present, in any of one or more appropriate layers of the photoconductor generally is in an amount from about 0.5 to about 25 weight percent and in some embodiments in an amount from about 1 to about 10 weight percent, based on the weight of the particular layer. Furthermore, the optional crosslinking agent, such as a cyclic acid anhydride, in the photoconductive layer can be, when present, in an amount from about 0.1 to about 16 weight percent and in further embodiments in an amount from about 1 to about 15 weight percent, based on the weight of the photoconductive layer. A person of ordinary skill in the art will recognize that additional ranges of compositions within the explicit ranges are contemplated and are within the present disclosure.

For example, the photoconductive layer may be formed by dispersing or dissolving the components, such as one or more of a charge generating compound, a charge transport compound, an electron transport compound, a UV light stabilizer, and a polymeric binder in organic solvent, coating the dispersion and/or solution on the respective underlying layer and drying the coating. In particular, the components can be dispersed by high shear homogenization, ball-milling, attritor milling, high energy bead (sand) milling or other size reduction processes or mixing means known in the art for effecting particle size reduction in forming a dispersion.

The photoreceptor may optionally have one or more additional layers as well. An additional layer can be, for example, a sub-layer or an overcoat layer, such as a barrier layer, a release layer, a protective layer, or an adhesive layer. A release layer forms the uppermost layer of the photoconductor element. A barrier layer may be sandwiched between the release layer and the photoconductive element or used to overcoat the photoconductive element. The barrier layer provides protection from abrasion and/or carrier liquid to the underlayers. An adhesive layer locates and improves the adhesion between a photoconductive element, a barrier layer and a release layer, or any combination thereof. A sub-layer is a charge blocking layer and locates between the electrically conductive substrate and the photoconductive element. The sub-layer may also improve the adhesion between the electrically conductive substrate and the photoconductive element.

Suitable barrier layers include, for example, coatings such as crosslinkable siloxanol-colloidal silica coating and hydroxylated silsesquioxane-colloidal silica coating, and organic binders such as polyvinyl alcohol, methyl vinyl ether/maleic anhydride copolymer, casein, polyvinyl pyrrolidone, polyacrylic acid, gelatin, starch, polyurethanes, polyimides, polyesters, polyamides, polyvinyl acetate, polyvinyl chloride, polyvinylidene chloride, polycarbonates, polyvinyl butyral, polyvinyl acetoacetal, polyvinyl formal, polyacrylonitrile, polymethyl methacrylate, polyacrylates, polyvinyl carbazoles, copolymers of monomers used in the above-mentioned polymers, vinyl chloride/vinyl acetate/vinyl alcohol terpolymers, vinyl chloride/vinyl acetate/maleic acid terpolymers, ethylene/vinyl acetate copolymers, vinyl chloride/vinylidene chloride copolymers, cellulose polymers, and mixtures thereof. The above barrier layer polymers optionally may contain small inorganic particles such as fumed silica, silica, titania, alumina, zirconia, or a combination thereof. Barrier layers are described further in U.S. Pat. No. 6,001,522 to Woo et al., entitled "Barrier Layer For Photoconductor Elements Comprising An Organic Polymer And Silica," incorporated herein by reference. The release layer topcoat may comprise any release layer composition known in the art. In some embodiments, the release layer is a fluorinated polymer, siloxane polymer, fluorosilicone polymer, silane, polyethylene, polypropylene, polyacrylate, or a combination thereof. The release layers can comprise crosslinked polymers.

The release layer may comprise, for example, any release layer composition known in the art. In some embodiments, the release layer comprises a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In further embodiments, the release layers comprise crosslinked polymers.

The protective layer can protect the organophotoreceptor from chemical and mechanical degradation. The protective layer may comprise any protective layer composition known in the art. In some embodiments, the protective layer is a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In some embodiments of particular interest, the release layers are crosslinked polymers.

The overcoat layer may comprise an electron transport compound as described further in copending U.S. patent application Ser. No. 10/396,536, filed on Mar. 25, 2003 to Zhu et al. entitled, "Organoreceptor With An Electron Transport Layer," incorporated herein by reference. For example, an electron transport compound as described above may be used in the release layer of this invention. The electron transport compound in the overcoat layer can be in an amount from about 2 to about 50 weight percent, and in other embodiments in an amount from about 10 to about 40 weight percent, based on the weight of the release layer. A person of ordinary skill in the art will recognize that additional ranges of composition within the explicit ranges are contemplated and are within the present disclosure.

Generally, adhesive layers comprise a film forming polymer, such as polyester, polyvinylbutyral, polyvinylpyrrolidone, polyurethane, polymethyl methacrylate, poly(hydroxy amino ether) and the like. Barrier and adhesive layers are described further in U.S. Pat. No. 6,180,305 to Ackley et al., entitled "Organic photoreceptors for liquid electrophotography," incorporated herein by reference.

Sub-layers can comprise, for example, polyvinylbutyral, organosilanes, hydrolyzable silanes, epoxy resins, polyesters, polyamides, polyurethanes, silicones and the like. In some embodiments, the sub-layer has a dry thickness between about 20 Angstroms and about 2,000 Angstroms. Sublayers containing metal oxide conductive particles can be between about 1 and about 25 microns thick. A person of ordinary skill in the art will recognize that additional ranges of compositions and thickness within the explicit ranges are contemplated and are within the present disclosure.

The charge transport compounds as described herein, and photoreceptors including these compounds, are suitable for use in an imaging process with either dry or liquid toner development. For example, any dry toners and liquid toners known in the art may be used in the process and the apparatus of this invention. Liquid toner development can be desirable because it offers the advantages of providing higher resolution images and requiring lower energy for image fixing compared to dry toners. Examples of suitable liquid toners are known in the art. Liquid toners generally comprise toner particles dispersed in a carrier liquid. The toner particles can comprise a colorant/pigment, a resin binder, and/or a charge director. In some embodiments of liquid toner, a resin to pigment ratio can be from 1:1 to 10:1, and in other embodiments, from 4:1 to 8:1. Liquid toners are described further in Published U.S. patent applications Ser. No. 2002/0128349, entitled "Liquid Inks Comprising A Stable Organosol," Ser. No. 2002/0086916, entitled "Liquid Inks Comprising Treated Colorant Particles," and Ser. No. 2002/0197552, entitled "Phase Change Developer For Liquid Electrophotography," all three of which are incorporated herein by reference.

Charge Transport Compound

This invention features an organophotoreceptor that comprises a charge transport compound having the formula (1)

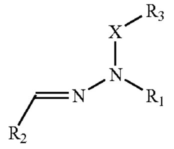

where X is a divalent hydrocarbon radical of less than 30 carbon atoms, or a divalent hydrocarbon radical of less than 30 carbon atoms where there is at least one substitution of a carbon atom by a heteroatom provided that no two heteroatoms may be adjacent within the backbone of an aliphatic divalent hydrocarbon radical, $R_1$ is an aryl group (e.g., phenyl group, naphthyl group, stilbenyl group, (9H-fluoren-9-ylidene)benzyl group, or tolanyl group) or a heterocyclic group, $R_2$ is a (N,N-disubstituted)arylamine group (e.g., a p-(N,N-disubstituted) arylamine group, such as a triphenylamine, a carbazole group or a julolidine group), and $R_3$ is an epoxy group.

In some embodiments, $R_2$ can be a divalent group that can bond with two hydrazone groups. Each hydrazone group can have the structure of equation (1), specifically —C═N—$NR_1$—X—$R_3$. However, the two hydrazone groups may or may not have an identical chemical structure. In particular, a carbazole group or a julolidine group can have two valences that are incorporated into the two hydrazone groups.

When the charge transport compounds with the structure of formula (1) are incorporated into the organophotoreceptor, the epoxy group can react with functional groups of the binder, for appropriate binders. Suitable polymer functional groups include, for example, hydroxyl, thiol, amino (primary amino or secondary amino), a carboxyl group or a combination thereof. Such crosslinking to the binder stabilizes the organophotoreceptor structure and distribution of charge transport compound within the structure. However, it is possible that the epoxy functionality is essentially eliminated by the reaction with the binder. Reaction of the epoxy functionality results in a particular chemical structure with a hydroxyl group at a position spaced by one carbon atom relative to a carbon atom bonded to an atom of the binder or crosslinking agent functional group that is involved in a nucleophylic addition at the epoxy functional group. Specifically, the resulting compound has a structure of Y—$CR_4R_6CR_5OH$—X, where Y is the bonded binder with or without a crosslinking agent. For convenience, the bonded epoxy functionality Y—$CR_4R_6CR_5OH$—X is referred to herein as an epoxy group along with the group that maintains the epoxy functionality with the bridging oxygen atom.

The divalent hydrocarbon group X may be aliphatic, aromatic, or mixed aliphaticaromatic. Non-limiting examples of aliphatic divalent hydrocarbon group are $—(CH_2)_m—$, $—(CHR)_n—$, or $—(CR'R'')_n$ where m and n are, independently, an integer between 1 and 20 and R, R', and R" are, independently, an alkyl group. Non-limiting examples of aromatic divalent hydrocarbon group have the following formulas:

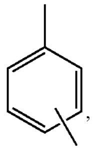,
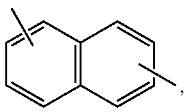,
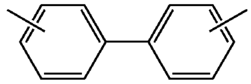.

Non-limiting examples of mixed aliphatic-aromatic divalent hydrocarbon group have the following formulas:

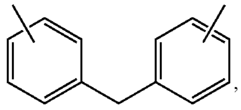,
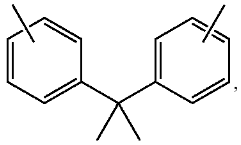, and other compounds can also include cyclic aliphatic groups.

The divalent hydrocarbon group X may also comprise a heteroatom such as N, S, and O, by substituting at least a carbon atom by a heteroatom provided that no two heteroatoms may be adjacent within the backbone of aliphatic divalent hydrocarbon groups. Non-limiting examples of such divalent hydrocarbon group have the following formulas:

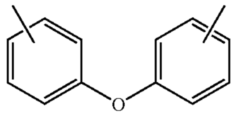
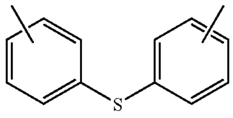
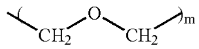

where m is an integer between 0 and 10.

The epoxy group $R_3$ has the following structure

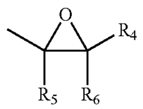

where the unlabeled bond corresponds to the bond to X, $R_4$ is hydrogen, alkyl group, or aromatic group, and $R_5$ and $R_6$ are, independently, hydrogen, alkyl group, aromatic group or, when fused together, the atoms necessary to form a 5-member, 6-member, or higher-member cycloaliphatic ring.

Specific, non-limiting examples of suitable charge transport compounds within the general formula (1) of the present invention have the following structures.

(2)
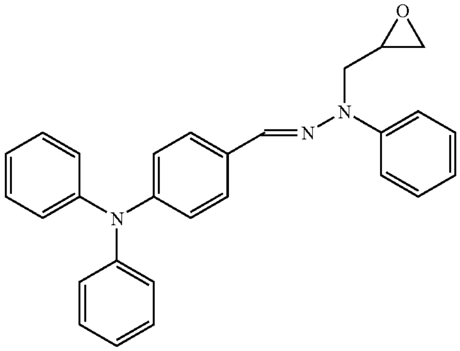
(3)
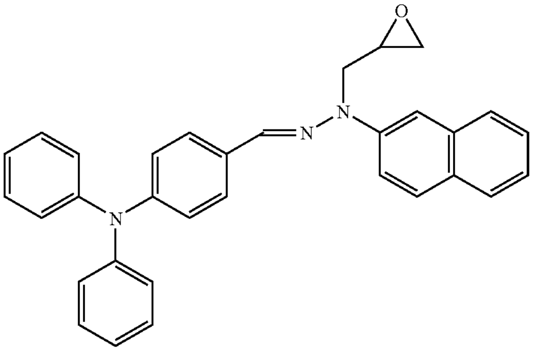
(4)
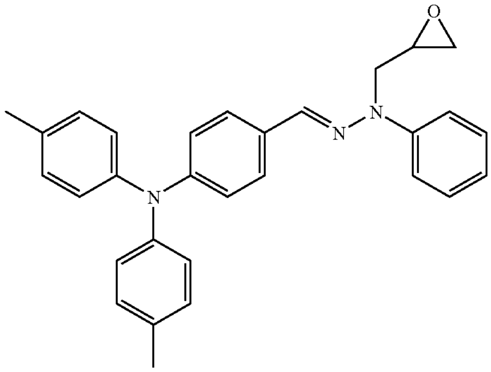
(5)
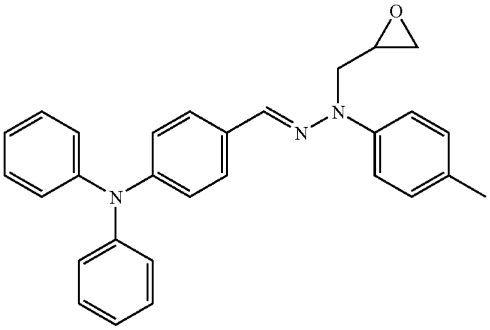
(6)
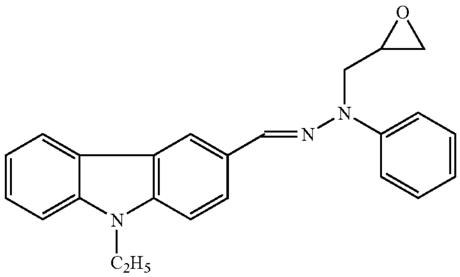
(7)
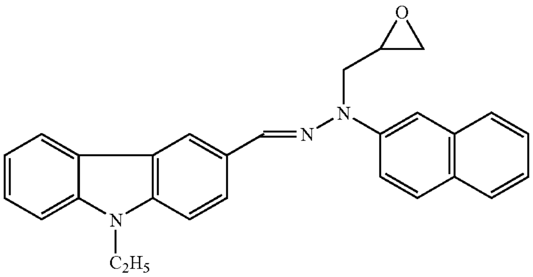
(8)
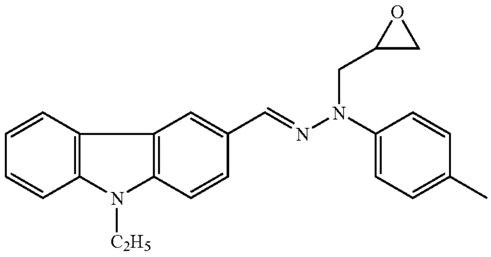
(9)
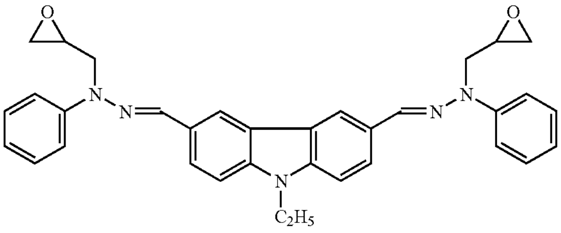
(10)
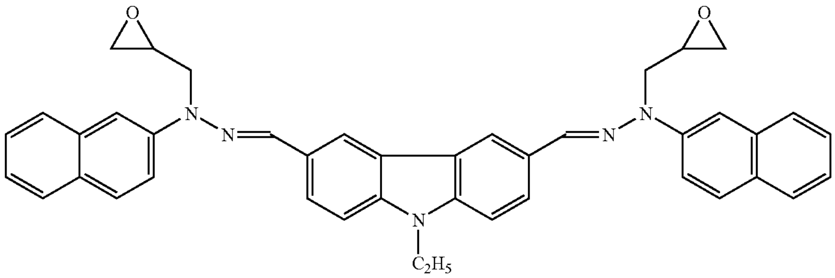

-continued (11)

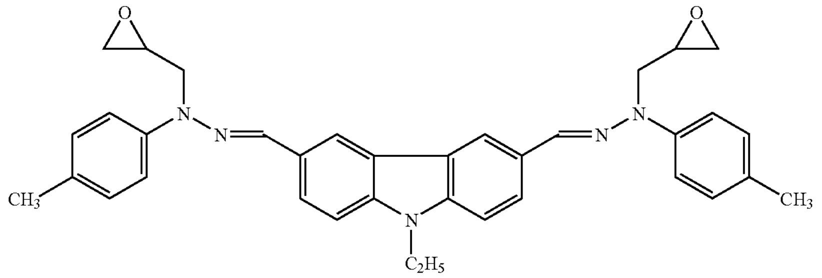

Synthesis of Charge Transport Compounds

The charge transport compounds with a hydrazone bonded to the epoxy group generally are synthesized by forming the desired substituted hydrazone which is reacted at the secondary amine to form the epoxy group with the selected X linking group. For example, the aromatic-substituted secondary amine reacts with the epichlorohydrin by way of the active hydrogen of the secondary amine in a base catalyzed reaction to form the epoxy group with a $—CH_2—$ group (as the X-group) between the epoxy group and the amine. Other X groups can be formed using appropriate bifunctional reactants as described further below. The hydrazone is formed from the reaction of an aryl substituted hydrazine with an aldehyde or ketone having a N,N-disubstituted arylamine.

The aromatic-substituted hydrazine supplies the $R_1$ group from formula (1) above, and an N,N-disubstituted amino aryl substituted aldehyde or ketone supplies the $R_2$ group of formula (1). In the reaction of the aldehyde or ketone with the hydrazine, the oxygen of the aldehyde/ketone group is replaced with the double bonded carbon.

While epichlorohydrin can be used to form the epoxy substituted compound with $X=—CH_2—$, alternatively other X groups can be formed, for example, using bifunctional group with a halogen and with a vinyl group (C═C) or substituted vinyl group. The halide group can be replaced by a bond to the secondary amine group of the hydrazone by a nucleophilic substitution. The vinyl or substituted vinyl group can be converted to the epoxy group in a epoxidation reaction, for example, by the reaction with perbenzoic acid or other peroxy acid, in an electrophilic addition reaction. Thus, the identity of X can be selected as desired through the introduction of a difunctional compound with a halide group and a vinyl/substituted-vinyl group.

As noted above, the epoxy groups can be reacted with functional groups of a polymer binder directly or through a crosslinking agent. The reactions of epoxy groups with appropriate functional groups are described further in C. A. May, editor, "Epoxy Resins Chemistry And Technology," (Marcel Dekker, New York, 1988) and in B. Ellis, editor, "Chemistry And Technology Of Epoxy Resins," (Blackie Academic And Professional, London, 1993), both of which are incorporated herein by reference.

Hydrazines

The syntheses of some representative hydrazines are described as follows.

1,1-Dinaphthylhydrazine 1,1-Dinaphthylhydrazine can be prepared according to the procedure described in Staschkow, L. I.; Matevosyan, R. O. Journal of the General Chemistry (1964) 34, 136, which is incorporated herein by reference. A suspension of 0.07 mole of the naphthyl nitrosamine in 750 ml of ether is cooled to 5–8° C. and treated with 150 g of zinc dust. Acetic acid (70 ml) is then added drop wise with stirring. To complete the reaction, 40 g of zinc dust is added. The reaction mixture is heated and filtered from the sludge. The mother liquor is washed with 10% sodium carbonate solution and dried with solid potassium hydroxide (KOH). The ether is distilled off to give the crystalline hydrazine, which is crystallized from ethanol or butanol. Other symmetric disubstituted hydrazines can be synthesized based on an equivalent process.

N-Phenyl-N-sulfolan-3-ylhydrazine

N-Phenyl-N-sulfolan-3-ylhydrazine can be prepared according to the procedure described in Great Britain Patent No. 1,047,525 by Mason, which is incorporated herein by reference. To a mixture of 0.5 mole of butadiene sulfone (commercially available from Aldrich, Milwaukee, Wis.) and 0.55 mole of phenylhydrazine (commercially available from Aldrich, Milwaukee, Wis.) was added 0.005 mole 40% aqueous potassium hydroxide solution. The mixture was kept for 2 hours at 60° C. whereupon a solid separated. After 10 hours the solid was filtered off to give N-phenyl-N-sulfolan-3-ylhydrazine (53%) having a melting point of 120–121° C. (recrystallized from methanol).

N-Pyrrol-2-yl-N-phenylhydrazine

N-Pyrrol-2-yl-N-phenylhydrazine can be prepared according to the procedure described in Japanese Patent No. 05148210 by Myamoto, incorporated herein by reference.

1-Phenyl-1-(1-benzyl-1H-tetrazol-5-yl)hydrazine

1-Phenyl-1-(1-benzyl-1H-tetrazol-5-yl)hydrazine can be prepared according to the procedure described in Tetrahedron (1983), 39(15), 2599–608 by Atherton et al., incorporated herein by reference.

N-(4-Stilbenyl)-N-phenylhydrazine

N-(4-Stilbenyl)-N-phenylhydrazine can be prepared according to the procedure described in Zh. Org. Khim. (1967), 3(9), 1605–3 by Matevosyan et al., incorporated herein by reference. Following this procedure, to a mixture of phenylhydrazine (97 g, 0.9 mole, commercially available from Aldrich, Milwaukee, Wis.) and p-chlorostilbene (21.4 g, 0.1 mole, commercially available from Spectrum Quality Products, Inc., Gardena, Calif.; Web: www.spectrumchemical.com) heated to boiling temperature, sodium was slowly added until there was no more discharge of red coloration. After boiling for some time the mixture was dissolved in 1750 ml of ethanol and cooled to −15° C. The precipitated product was recrystallized to give 28% of N-(4-stilbenyl)-N-phenylhydrazine.

N-(5-Benzotriazolyl)-N-phenylhydrazine

N-(5-benzotriazolyl)-N-phenylhydrazine can be prepared according to the procedure that follows. To a mixture of phenylhydrazine (97 g, 0.9 mole, commercially available from Aldrich, Milwaukee, Wis.) and 5-chlorobenzotriazole (15.4 g, 0.1 mole, commercially available from Aldrich, Milwaukee, Wis.) heated to boiling temperature, sodium is slowly added until there is no more discharge of red coloration. After boiling for some time the mixture is cooled to room temperature. The product is isolated and purified.

N-Phenyl-N-sulfolan-3-ylhydrazine

N-Phenyl-N-sulfolan-3-ylhydrazine can be prepared according to the procedure described in Great Britain Patent No. 1,047,525 by Mason, incorporated herein by reference. Following this procedure, to a mixture of 0.5 mole of butadiene sulfone (commercially available from Aldrich, Milwaukee, Wis.) and 0.55 mole of phenylhydrazine (commercially available from Aldrich, Milwaukee, Wis.), a 0.005 mole 40% aqueous potassium hydroxide solution was added. The mixture was kept for 2 hours at 60° C. whereupon a solid separated. After 10 hours the solid was filtered off to give N-phenyl-N-sulfolan-3-ylhydrazine (I) (93%) having a melting point of 119–120° C. (recrystallized from methanol).

N-4-[(9H-fluoren-9-ylidene)benzyl]-N-phenylhydrazine

N-4-[(9H-fluoren-9-ylidene)benzyl]-N-phenylhydrazine can be prepared according to the procedure similar to that described in Zh. Org. Khim. (1967), 3(9), 1605–1613 by Matevosyan et al., incorporated herein by reference. Following this procedure, to a mixture of phenylhydrazine (97 g, 0.9 mole, commercially available from Aldrich, Milwaukee, Wis.) and p-9-(4-chlorobenzylidene)fluorene (28.9 g, 0.1 mole, commercially available from Aldrich, Milwaukee, Wis.) heated to boiling temperature, sodium was slowly added until there was no more discharge of red coloration. After boiling for some time the mixture was dissolved in 1750 ml of ethanol and cooled to −15° C. The precipitated product was recrystallized to give N-4-[(9H-fluoren-9-ylidene)benzyl]-N-phenylhydrazine.

5-Methyl-1-Phenyl-3-(1-Phenylhydrazino)-Pyrazole

5-Methyl-1-phenyl-3-(1-phenylhydrazino)-pyrazole can be prepared according to the procedure described in J. Chem. Soc. C (1971), (12), 2314–17 by Boyd et al., incorporated herein by reference.

4-Methylsulfonylphenylhydrazine (Registry Number 877-66-7)

4-Methylsulfonylphenylhydrazine is commercially available from Fisher Scientific USA, Pittsburgh, Pa. (1-800-766-7000).

1,1'-(Sulfonyldi-4,1-phenylene)bishydrazine (Registry Number 14052-65-4)

1,1'-(Sulfonyldi-4,1-phenylene)bishydrazine dihydrochloride is commercially available from Vitas-M, Moscow, Russia; (Phone: +7(095) 939-5737)

Arylaldehydes

Representative arylaldehydes for reacting with the hydrazones can be obtained as follows.

Synthesis of Julolidine Aldehyde

Julolidine (100 g, 0.6 moles, commercially obtained from Aldrich Chemicals Co, Milwaukee, Wis. 53201) was dissolved in dimethylformamide (DMF) (200 ml, commercially obtained from Aldrich) in a 500 ml three neck round bottom flask. The flask was cooled to 0° C. in ice bath. $POCl_3$ (107 g, 0.7 mole, Aldrich) was added drop wise while keeping the temperature below 5° C. After the addition of $POCl_3$ was completed, the flask was warmed to room temperature and placed in a steam bath while stirring for a period of 1 hour. The flask was cooled to room temperature and the solution was added slowly to a large excess of distilled water with good agitation. Stirring was continued for additional 2 hours. The solid was filtered off and washed repeatedly with water until the effluent water became neutral. The product was dried in vacuum oven at 50° C. for 4 hours.

Other Aryl Aldehydes

Suitable commercially available (N,N-disubstituted)arylamine aldehydes are available form Aldrich (Milwaukee, Wis.) including, for example, diphenylamino-benzaldehyde ($(C_6H_5)_2NC_6H_4CHO$) and 9-ethyl-3-carbazolecarboxyaldehyde. Also, the synthesis of N-ethyl-3,6-diformylcarbazole is described below in the examples.

Synthesis of Hydrazones

A hydrazine can be reacted with an appropriate aromatic aldehyde or ketone to form a desired hydrazone charge transfer compound. The reactions can be catalyzed by an appropriate amount of concentrated acid, in particular sulfuric acid. After mixing in the catalytic amount of acid with the hydrazine and aromatic aldehyde, the mixture can be refluxed for about 2 hours to about 16 hours. The initial product can be purified by recrystallization. The synthesis of selected compounds from the formulas above are described below in the Examples, and the other compounds described herein can be similarly synthesized.

In some embodiments, the hydrazines may be obtained in an acidified hydrochloride form, as noted above. For these embodiments, the hydrazine hydrochloride can be reacted with an aqueous carbonate base while stirring the mixture. An excess of carbonate base can be added, such as 1.2 moles of potassium carbonate for embodiments with one mole of hydrazine hydrochloride per mole hydrazine or 2.4 moles of potassium carbonate for embodiments with one mole of hydrazine dihydrochloride per mole hydrazine. Some specific examples are presented below.

Reactions with a Crosslinking Agent

In general, the charge transport compound is combined with the binder and any other components of the particular layer of the organophotoreceptor for forming the particular layer. If a crosslinking agent is used, it may be desirable to react the crosslinking agent first with either the charge transport compound or with the polymer binder before combining the other ingredients. A person of ordinary skill in the art can evaluate the appropriate reaction order, such as combining all of the components at one time or sequentially, for forming the layer with desired properties.

The invention will now be described further by way of the following examples.

EXAMPLES

Example 1

Preparation of Charge Transfer Compounds

This example describes the synthesis of three charge transfer compounds described above. Specifically, the synthesis of compounds 2, 4, 6, and 9 corresponding to the formulas above is described.

Preparation of 4-(Diphenylamino)benzaldehyde-N-2, 3-epoxypropyl-N-Phenylhydrazone (Compound 2)

Phenylhydrazine (0.1 mole, commercially available from Aldrich, Milwaukee, Wis.) and 4-(Diphenylamino) benzaldehyde (0.1 mole, available from Fluka, Buchs SG, Switzerland) were dissolved in 100 ml of isopropanol in a 250 ml 3-neck round bottom flask equipped with reflux condenser and mechanical stirrer. The solution was refluxed for 2 hours. Thin layer chromatography indicated the disappearance of the starting materials. At the end of the reaction, the mixture was cooled to room temperature. The 4-(diphenylamino) benzaldehyde phenylhydrazone crystals that formed upon standing were filtered off and washed with isopropanol and dried in vacuum oven at 50° C. for 6 hours.

A mixture of 4-(diphenylamino) benzaldehyde phenylhydrazone (3.6 g , 0.01 mole), 85% powdered potassium hydroxide (2.0 g , 0.03 mole) and anhydrous potassium carbonate in 25 ml of epichlorohydrin was stirred vigorously at 55–60° C. for 1.5–2 hours. The course of the reaction was monitored using thin layer chromatography on silica gel 60 F254 plates (commercially available from Merck, Whitehouse Station, N.J.) using 1:4 v/v mixture of acetone and hexane as eluant. After termination of the reaction, the mixture was cooled to room temperature, diluted with ether, and washed with water until the wash water had a neutral pH. The organic layer was dried over anhydrous magnesium sulfate, treated with activated charcoal and filtered. Ether was removed and the residue was dissolved in a 1:1 volume per volume mixture of toluene and isopropanol. The crystals formed upon standing were filtered off and washed with isopropanol to give 3.0 g of product (71.4% yield) with a melting point of 141–142.5° C. The product was recrystallized from a 1:1 mixture of toluene and isopropanol. The product was characterized with $^1$H-NMR in $CDCl_3$ (250 MHz instrument) with peaks observed at the following delta values in ppm:—7.65–6.98 (m, 19H), 6.93 (t, J=7.2 Hz, 1H), 4.35 (dd, 1H), 3.99 (dd, 1H), 3.26 (m, 1H), 2.84 (dd, 1H), 2.62 (dd, 1H). An elemental analysis yielded the following results in weight percent: % C=80.02, % H=6.31, % N=9.91, which compares with calculated values for $C_{28}H_{25}N_3O$ of % C=80.16, % H=6.01, % N=10.02.

Preparation of 4-(4,4'-dimethyldiphenylamino)benzaldehyde-N-2,3-epoxypropyl-N-phenylhydrazone (Compound 4)

Phenylhydrazine (0.1 mole, commercially available from Aldrich, Milwaukee, Wis.) and 4-(4,4'-dimethyldiphenylamino)benzaldehyde (0.1 mole, available from Syntec GmbH, Germany) were dissolved in 100 ml of isopropanol in a 250 ml 3-neck round bottom flask equipped with reflux condenser and mechanical stirrer. The solution was refluxed for 2 hours. Thin layer chromatography indicated the disappearance of the starting materials. At the end of the reaction, the mixture was cooled to room temperature. The 4-(4,4'-dimethyldiphenylamino)benzaldehyde phenylhydrazone crystals that formed upon standing were filtered off and washed with isopropanol and dried in vacuum oven at 50° C. for 6 hours.

A mixture of 4-(4,4'-dimethyldiphenylamino)benzaldehyde phenylhydrazone (3.9 g , 0.01 mole), 85% powdered potassium hydroxide (2.0 g , 0.03 mole) and anhydrous potassium carbonate in 25 ml of epichlorohydrin was stirred vigorously at 55–60° C. for 1.5–2 hours. The course of the reaction was monitored using thin layer chromatography on silica gel 60 F254 plates (commercially available from Merck, Whitehouse Station, N.J.) using 1:4 v/v mixture of acetone and hexane as eluant. After termination of the reaction, the mixture was cooled to room temperature, diluted with ether, and washed with water until the wash water had a neutral pH. The organic layer was dried over anhydrous magnesium sulfate, treated with activated charcoal and filtered. Ether was removed and the residue was purified by crystallization from toluene followed by column chromatography (silica gel Merck grade 9385, 60 Å, Aldrich; 4:1 v/v solution of hexane and acetone as the eluant). The yield of compound 4 was 65.5%. The product was characterized with $^1$H-NMR spectrum. The product was characterized with $^1$H-NMR in $CDCl_3$ (400 MHz instrument) with peaks observed at the following delta values in ppm:—7.62 (s, 1H), 7.55–6.90 (m, 17H)' 4.35 (dd, 1H), 3.98 (dd, 1H), 3.27 (m, 1H), 2.85 (dd, 1H), 2.63 (dd, 1H), 2.32 (s, 6H). An elemental analysis yielded the following results in weight percent: % C=80.42, % H=6.41, % N=9.21, which compares with calculated values for $C_{30}H_{29}N_3O$ of % C=80.51, % H=6.53, % N=9.39.

Preparation of Compound 6

Phenylhydrazine (0.1 mole, commercially available from Aldrich, Milwaukee, Wis.) and 9-ethyl-3-carbazolecarboxaldehyde (0.1 mole, available from Aldrich Chemical, Milwaukee, Wis.) were dissolved in 100 ml of isopropanol in 250 ml 3-neck round bottom flask equipped with a reflux condenser and a mechanical stirrer. The solution was refluxed for 2 hours. Thin layer chromatography indicated the disappearance of the starting materials. At the end of the reaction, the mixture was cooled to room temperature. The 9-ethyl-3-carbazolecarbaldehyde phenylhydrazone crystals formed upon standing were filtered off and washed with isopropanol and dried in vacuum oven at 50° C. for 6 hours.

A mixture of 9-ethyl-3-carbazolecarbaldehyde phenylhydrazone (3.1 g, 0.01 mole), 85% powdered potassium hydroxide (2.0 g, 0.03 mole) and anhydrous potassium carbonate in 25 ml of epichlorohydrin was stirred vigorously at 55–60° C. for 1.5–2 hours. The course of the reaction was monitored using thin layer chromatography on silica gel 60 F254 plates (commercially available from Merck) using 1:4 v/v mixture of acetone and hexane as eluant. After termination of the reaction, the mixture was cooled to room temperature, diluted with ether and washed with water until the wash water had a neutral pH. The organic layer was dried over anhydrous magnesium sulfate, treated with activated charcoal and filtered. Ether was removed and the residue was dissolved in a 1:1 mixture of toluene and isopropanol. The crystals formed upon standing were filtered off and washed with isopropanol to give 3.0 g of product (81.2% yield) with a melting point of 136–137° C. The product was recrystallized from 1:1 mixture of toluene and isopropanol. The product was characterized with $^1$H-NMR in $CDCl_3$ (250 MHz) which yielded peaks at the following delta values in ppm:—8.35 (s, 1H), 8.14 (d, J=7.8 Hz, 1H), 7.93 (d, J=7.6 Hz, 1H), 7.90 (s, 1H), 7.54–7.20 (m, 8H), 6.96 (t, J=7.2 Hz , 1H), 3H), 4.04 (dd, J1=4.3 Hz, J2=16.4 Hz, 1H), 3.32 (m, 1H), 2.88 (dd, 1H), 2.69 (dd, 1H), 1.44 (t, J=7.2 Hz, 3H). Elemental analysis yielded the following results in weight percent % C=78.32, % H=6.41, % N=11.55; which compares with calculated values for $C_{24}H_{23}N_3O$ of % C=78.02, % H=6.28, N %=11.37.

Preparation of Compound 9

A 271 ml quantity of DMF (3.5 mol) was added to a 1-liter, 3-neck round bottom flask equipped with a mechanical stirrer, a thermometer, and an addition funnel. The contents were cooled in a salt/ice bath. When the temperature inside the flask reached 0° C., 326 ml of $POCl_3$ (3.5 mol) was slowly added. During the addition of $POCl_3$, the temperature inside the flask was not allowed to rise above 5° C. After the addition of $POCl_3$, the reaction mixture was allowed to warm to room temperature. After the flask warmed to room temperature, N-ethylcarbazole (93 g) in 70 ml of DMF was added, and then the flask was heated to 90° C. for 24 hours using a heating mantle. Then, the reaction mixture was cooled to room temperature, and the reaction mixture was added slowly to a cooled 4.5 liter beaker containing a solution comprising 820 g of sodium acetate dissolved in 2 liters of water. The beaker was cooled in an ice bath and stirred for 3 hours. The brownish solid obtained was filtered and washed repeatedly with water, followed by a small amount of ethanol (50 ml). After washing, the resulting product was recrystallized once from toluene using activated charcoal and dried under vacuum in an oven heated at 70° C. for 6 hours to obtain 55 g (46% yield) of N-ethyl-3,6-diformylcarbazole. The product was characterized with $^1$H-NMR (250 Hz, in $CDCl_3$) to obtain the following delta values in ppm: 10.12 (s, 2H), 8.63 (s, 2H), 8.07 (d, 2H), 7.53 (d, 2H), 4.45 (m, 2H), 1.53 (t, 3H).

Phenylhydrazine (0.2 mole, commercially available from Aldrich, Milwaukee, Wis.) and N-ethyl-3,6-diformylcarbazole (0.1 mole) were dissolved in 100 ml of a 1:1 mixture of toluene and THF in 250 ml 3-neck round bottom flask equipped with a reflux condenser and a mechanical stirrer. The solution was refluxed for 2 hours. Thin layer chromatography indicated the disappearance of the starting materials. At the end of the reaction, the mixture was cooled to room temperature. The N-ethyl-3,6-diformylcarbazole bis (N-phenylhydrazone) crystals formed upon standing were filtered off, washed with isopropanol and dried in vacuum oven at 50° C. for 6 hours. Without further purification, the product was used for the next step.

A mixture of N-ethyl-3,6-diformylcarbazole bis(N-phenylhydrazone) (4.3 g, 0.01 mole), 85% powdered potassium hydroxide (2.0 g, 0.03 mole) and anhydrous potassium carbonate in 25 ml of epichlorohydrin was stirred vigorously at 55–60° C. for 1.5–2 hours. The course of the reaction was monitored using thin layer chromatography on silica gel 60 F254 plates (commercially available from Merck) using a 1:4 by volume mixture of acetone and hexane as eluant. After termination of the reaction, the mixture was cooled to room temperature, diluted with ether, and washed with water until the wash water had a neutral pH. The organic layer was dried over anhydrous magnesium sulfate, treated with activated charcoal and filtered. Ether was removed and the residue was purified by crystallization from toluene followed by column chromatography (silica gel Merck grade 9385, 60 Å, Aldrich; 4:1 v/v solution of hexane and acetone as the eluant). The yield of compound 9 was 68.5%, and the product had a melting point of 119–120° C. (recrystallized from toluene). The product was characterized with $^1$H NMR spectrum (100 MHz, $CDCl_3$), which yielded the following delta values in ppm: 8.5–7.8 (m, 8H), 7.6–7.2 (m, 8H), 7.0 (m, 2H), 4.55 (m, 6H), 3.3 (m, 2H), 2.9 (dd, 2H), 2.65 (dd, 2H), 1.4 (t, 3H). An elemental analysis yielded the following values in weight %: C 75.01; H 6.91; N 12.68. For comparison the calculated elemental weight percents for $C_{41}H_{46}N_6O_2$ are %: C 75.20; H 7.08; N 12.83.

Example 2

Preparation of an Electron Transport Compound

This example describes the preparation of (4-n-butoxycarbonyl-9-fluorenylidene) malononitrile.

A 460 g quantity of concentrated sulfuric acid (4.7 moles, analytical grade, commercially obtained from Sigma-Aldrich, Milwaukee, Wis.) and 100 g of diphenic acid (0.41 mole, commercially obtained from Acros Fisher Scientific Company Inc., Hanover Park, Ill.) were added to a 1-liter 3-neck round bottom flask, equipped with a thermometer, mechanical stirrer and a reflux condenser. Using a heating mantle, the flask was heated to 135–145° C. for 12 minutes, and then cooled to room temperature. After cooling to room temperature, the solution was added to a 4-liter Erlenmeyer flask containing 3 liter of water. The mixture was stirred mechanically and was boiled gently for one hour. A yellow solid was filtered out hot, washed with hot water until the pH of the wash-water was neutral, and dried in the air overnight. The yellow solid was fluorenone-4-carboxylic acid. The yield was 75 g (80%). The product was then characterized. The melting point (m.p.) was found to be 223–224° C. A $^1$H-NMR spectrum of fluorenone-4-carboxylic acid was obtained in $d_6$-DMSO solvent with a 300 MHz NMR from Bruker Instrument. The peaks were found at (ppm) δ=7.39–7.50 (m, 2H), δ=7.79–7.70 (q, 2H), δ=7.74–7.85 (d, 1H), δ=7.88–8.00 (d, 1H), and δ=8.18–8.30 (d, 1H), where d is doublet, t is triplet, m is multiplet; dd is double doublet, q is quintet.

A 70 g (0.312 mole) quantity of fluorenone-4-carboxylic acid, 480 g (6.5 mole) of n-butanol (commercially obtained from Fisher Scientific Company Inc., Hanover Park, Ill.), 1000 ml of toluene and 4 ml of concentrated sulfuric acid were added to a 2-liter round bottom flask equipped with a mechanical stirrer and a reflux condenser with a Dean Stark apparatus. With aggressive agitation and refluxing, the solution was refluxed for 5 hours, during which about 6 g of water were collected in the Dean Stark apparatus. The flask was cooled to room temperature. The solvents were evaporated, and the residue was added, with agitation, to 4 liters of a 3% sodium bicarbonate aqueous solution. The solid was filtered off, washed with water until the pH of the wash-water was neutral, and dried in the hood overnight. The product was n-butyl fluorenone-4carboxylate ester. The yield was 70 g (80%). A $^1$H-NMR spectrum of n-butyl fluorenone-4-carboxylate ester was obtained in $CDCl_3$ with a 300 MHz NMR from Bruker Instrument. The peaks were found at (ppm) δ=0.87–1.09 (t, 3H), δ=1.42–1.70 (m, 2H), δ=1.75–1.88 (q, 2H), δ=4.26–4.64 (t, 2H), δ=7.29–7.45 (m, 2H), δ=7.46–7.58 (m, 1H), δ=7.60–7.68 (dd, 1H), δ=7.75–7.82 (dd, 1H), δ=7.90–8.00 (dd, 1H), δ=8.25–8.35 (dd, 1H).

A 70 g (0.25 mole) quantity of n-butyl fluorenone-4-carboxylate ester, 750 ml of absolute methanol, 37 g (0.55 mole) of malononitrile (commercially obtained from Sigma-Aldrich, Milwaukee, Wis.), 20 drops of piperidine (commercially obtained from Sigma-Aldrich, Milwaukee, Wis.) were added to a 2-liter, 3-neck round bottom flask equipped with a mechanical stirrer and a reflux condenser. The solution was refluxed for 8 hours, and the flask was cooled to room temperature. The orange crude product was filtered, washed twice with 70 ml of methanol and once with 150 ml of water, and dried overnight in the hood. This orange crude product was recrystallized from a mixture of 600 ml of acetone and 300 ml of methanol using activated charcoal. The flask was placed at 0° C. for 16 hours. The crystals were filtered and dried in a vacuum oven at 50 ° C. for 6 hours to obtain 60 g of pure (4-n-butoxycarbonyl-9-fluorenylidene) malononitrile. The melting point (m.p.) of the solid was found to be 99–100° C. A $^1$H-NMR spectrum of (4-n-butoxycarbonyl-9-fluorenylidene) malononitrile was obtained in $CDCl_3$ with a 300 MHz NMR from Bruker Instrument. The peaks were found at (ppm) δ=0.74–1.16 (t, 3H), δ=1.38–1.72 (m, 2H), δ=1.70–1.90 (q, 2H), δ=4.29–4.55 (t, 2H), δ=7.31–7.43 (m, 2H), δ=7.45–7.58 (m, 1H), δ=7.81–7.91 (dd, 1H), δ=8.15–8.25 (dd, 1H), δ=8.42–8.52 (dd, 1H), δ=8.56–8.66 (dd, 1H).

Example 3

Forming Organophotoreceptors

This example describes the formation of fifteen organophotoreceptor samples incorporating the charge transfer compounds of Example 1. These organophotoreceptors are characterized in the following examples. Furthermore, the formation of five comparative samples is described.

Sample 1

Sample 1 was a single layer organophotoreceptor having a 76.2 micron (3 mil) thick polyester substrate with a layer of vapor-coated aluminum (commercially obtained from CP Films, Martinsville, Va.). The coating solution for the single layer organophotoreceptor was prepared by combining 1.87 g of compound 2, 0.54 g of a (4-n-butoxycarbonyl-9-fluorenylidene) malononitrile, and 9.37 g of tetrahydrofuran, which were shaken until the components dissolved. A 7.4 g quantity of a 14 wt % polyvinyl butyral resin (BX-1, commercially obtained from Sekisui Chemical Co. Ltd., Japan) in tetrahydrofuran pre-mix solution and 0.83 g of a CGM mill-base containing 18.5 wt % of titanyl oxyphthalocyanine plus polyvinyl butyral resin at a weight ratio of 2.3:1 (BX-5, commercially obtained from Sekisui Chemical Co. Ltd., Japan) in tetrahydrofuran were added to the coating solution.

The CGM mill-base was obtained by milling 112.7 g of titanyl oxyphthalocyanine (commercially obtained from H.W. Sands Corp., Jupiter, Fla.) with 49 g of the polyvinyl butyral resin (BX-5) in 651 g of methylethylketone on a horizontal sand mill (model LMC12 DCMS, commercially obtained from Netzsch Incorporated, Exton, Pa.) with 1-micron zirconium beads using recycle mode for 4 hours.

After mixing the solution on a mechanical shaker for about 1 hour, the single layer coating solution was coated onto the substrate described above using a knife coater with a 94 micron orifice followed by drying in an oven at 110° C. for 5 minutes.

Sample 2

A single layer organophotoreceptor coating solution for forming sample 2 was prepared by combining 1.87 g of compound 2, 0.54 g of a (4-n-butoxycarbonyl-9-fluorenylidene) malononitrile, and 9.37 g of tetrahydrofuran, which were shaken until the components dissolved. A 7.4 g of a 14 wt % polyvinyl butyral resin (BX-1, commercially obtained from Sekisui Chemical Co. Ltd., Japan) in tetrahydrofuran pre-mix solution, 0.65 g of phthalic anhydride (Aldrich Chemical) in 3.0 g of tetrahydrofuran, and 0.83 g of a CGM mill-base containing 18.5 wt % of titanyl oxyphthalocyanine plus polyvinyl butyral resin at a weight ratio of 2.3:1 (BX-5, commercially obtained from Sekisui Chemical Co. Ltd., Japan) in tetrahydrofuran were added to the coating solution. The CGM mill-base was prepared as described for sample 1.

After mixing the solution on a mechanical shaker for about 1 hour, the single layer coating solution was coated onto an equivalent substrate as described for sample 1 using a knife coater with a 94 micron orifice followed by drying in an oven at 110° C. for 5 minutes.

Sample 3

A single layer organophotoreceptor coating solution for forming sample 3 was prepared by combining 1.87 g of compound 2, 0.54 g of a (4-n-butoxycarbonyl-9-fluorenylidene) malononitrile, and 9.37 g of tetrahydrofuran, which were shaken until the components dissolved. A 7.4 g quantity of a 14 wt % polyvinyl butyral resin (BX-1, commercially obtained from Sekisui Chemical Co. Ltd., Japan) in tetrahydrofuran premix solution, 0.43 g of maleic anhydride (Aldrich Chemical) in 2.0 g of tetrahydrofuran, and 0.83 g of a CGM mill-base containing 18.5 wt % of titanyl oxyphthalocyanine plus polyvinyl butyral resin at a ratio of 2.3:1 (BX-5, commercially obtained from Sekisui Chemical Co. Ltd., Japan) in tetrahydrofuran were added to this mixture. The CGM mill-base was prepared as described for sample 1.

After mixing the solution on a mechanical shaker for about 1 hour, the single layer coating solution was coated onto an equivalent substrate as described for sample 1 using a knife coater with a 94 micron orifice followed by drying in an oven at 110° C. for 5 minutes.

Sample 4

A single layer organophotoreceptor coating solution for forming sample 4 was prepared by combining 1.59 g of compound 2, 2.29 g of a 20 wt % (4-n-butoxycarbonyl-9-fluorenylidene) malononitrile in tetrahydrofuran pre-mix solution, 4.0 g of tetrahydrofuran, 7.91 g of a 11.1 wt % polyvinyl butyral resin (BX-5, commercially obtained from Sekisui Chemical Co. Ltd., Japan) in tetrahydrofuran pre-mix solution, and 0.7 g of a CGM mill-base containing 18.7 wt % of titanyl oxyphthalocyanine plus polyvinyl butyral resin at a ratio of 2.3:1 (BX-5, commercially obtained from Sekisui Chemical Co. Ltd., Japan) in tetrahydrofuran. The CGM mill-base was prepared as described for sample 1.

After mixing the solution on a mechanical shaker for about 1 hour, 0.5 g of a 10 wt % triethylamine solution in tetrahydrofuran was added, the coating solution was briefly shaken, and then coated onto an equivalent substrate as described for sample 1 using a knife coater with a 94 micron orifice followed by drying in an oven at 85° C. for 15 minutes.

Sample 5

A single layer organophotoreceptor coating solution for preparing sample 5 was prepared by combining 1.33 g of compound 2, 1.91 g of a 20 wt % (4-n-butoxycarbonyl-9-fluorenylidene) malononitrile in tetrahydrofuran pre-mix solution, 0.5 g of phthalic anhydride (Aldrich Chemical) in 5.5 g of tetrahydrofuran, 6.6 g of a 11.1 wt % polyvinyl butyral resin (BX-5, commercially obtained from Sekisui Chemical Co. Ltd., Japan) in tetrahydrofuran pre-mix solution, and 0.7 g of a CGM mill-base containing 18.7 wt % of titanyl oxyphthalocyanine plus polyvinyl butyral resin at a ratio of 2.3:1 (BX-5, commercially obtained from Sekisui Chemical Co. Ltd., Japan) in tetrahydrofuran. The CGM mill-base was prepared as described for sample 1.

After mixing the solution on a mechanical shaker for about 1 hour, 0.5 g of a 10 wt % triethylamine solution in tetrahydrofuran was added, the coating solution was briefly shaken, and then coated onto an equivalent substrate as described for sample 1 using a knife coater with a 94 micron orifice followed by drying in an oven at 85° C. for 15 minutes.

Sample 6

Sample 6 was prepared as described above for sample 1 except that 1.87 g of compound 6 was substituted for compound 2.

Sample 7

Sample 7 was prepared as described above for sample 2 except that 1.87 g of compound 6 was substituted for compound 2, and 0.75 g of phthalic anhydride in 3.4 g of tetrahydrofuran was added instead of the amounts listed for sample 2.

Sample 8

Sample 8 was prepared as described above for sample 3 except that 1.87 g of compound 6 was substituted for the compound 2 and that 0.5 g of maleic anhydride in 2.3 g of tetrahydrofuran was added instead of the amounts of maleic anhydride listed for sample 3.

Sample 9

Sample 9 was prepared as described above for sample 4 except that 1.59 g of compound 6 was substituted for compound 2.

Sample 10

Sample 10 was prepared as described above for sample 5 except that 1.33 g of compound 6 was substituted for compound 2.

Sample 11

Sample 11 was prepared as described above for sample 1 except that 1.87 g of compound 9 was substituted for compound 2.

Sample 12

Sample 12 was prepared as described above for sample 2 except that 1.87 g of compound 9 was substituted for compound 2, and 1.1 g of phthalic anhydride in 5.0 g of tetrahydrofuran was added instead of the amounts listed for sample 2.

Sample 13

Sample 13 was prepared as described above for sample 3 except that 1.87 g of compound 9 was substituted for the compound 2 and that 0.7 g of maleic anhydride in 3.2 g of tetrahydrofuran was added instead of the amounts of maleic anhydride listed for sample 3.

Sample 14

Sample 14 was prepared as described above for sample 4 except that 1.59 g of compound 9 was substituted for compound 2.

Sample 15

Sample 15 was prepared as described above for sample 5 except that 1.33 g of compound 9 was substituted for compound 2.

Comparative Sample A

To form comparative sample A, a single layer organophotoreceptor coating solution was prepared by combining 1.87 g of MPCT-10 (a charge transfer material, commercially obtained from Mitsubishi Paper Mills, Tokyo, Japan), 0.54 g of a (4-n-butoxycarbonyl-9-fluorenylidene) malononitrile, and 9.37 g of tetrahydrofuran, which was shaken until the components dissolved. A 7.4 g quantity of a 14 wt % polyvinyl butyral resin (BX-1, commercially obtained from Sekisui Chemical Co. Ltd., Japan) in tetrahydrofuran pre-mix solution and 0.83 g of a CGM mill-base containing 18.5 wt % of titanyl oxyphthalocyanine plus polyvinyl butyral resin at a ratio of 2.3:1 (BX-5, commercially obtained from Sekisui Chemical Co. Ltd., Japan) in tetrahydrofuran were added to the coating solution. The CGM mill-base was prepared as described for sample 1.

After mixing the solution on a mechanical shaker for about 1 hour, the single layer coating solution was coated onto an equivalent substrate as described for sample 1 using a knife coater with a 94 micron orifice followed by drying in an oven at 110° C. for 5 minutes.

Comparative Sample B

To form comparative sample B, a single layer organophotoreceptor coating solution was prepared by combining 1.87 g of MPCT-10 (a charge transfer material, commercially obtained from Mitsubishi Paper Mills, Tokyo, Japan), 0.54 g of a (4-n-butoxycarbonyl-9-fluorenylidene) malononitrile, and 9.37 g of tetrahydrofuran, which was shaken until the components dissolved. A 7.4 g quantity of a 14 wt % polyvinyl butyral resin (BX-1, commercially obtained from Sekisui Chemical Co. Ltd., Japan) in tetrahydrofuran pre-mix solution, 0.65 g of phthalic anhydride (Aldrich Chemical) in 3.0 g of tetrahydrofuran, and 0.83 g of a CGM mill-base containing 18.5 wt % of titanyl oxyphthalocyanine plus polyvinyl butyral resin at a ratio of 2.3:1 (BX-5, commercially obtained from Sekisui Chemical Co. Ltd., Japan) in tetrahydrofuran were added to the coating solution. The CGM mill-base was prepared as described for sample 1.

After mixing the solution on a mechanical shaker for about 1 hour, the single layer coating solution was coated onto an equivalent substrate as described for sample 1 using a knife coater with a 94 micron orifice followed by drying in an oven at 110° C. for 5 minutes.

Comparative Sample C

To form comparative sample C, a single layer organophotoreceptor coating solution was prepared by combining 1.87 g of MPCT-10 (a charge transfer material, commercially obtained from Mitsubishi Paper Mills, Tokyo, Japan), 0.54 g of a (4-n-butoxycarbonyl-9-fluorenylidene) malononitrile, and 9.37 g of tetrahydrofuran, which was shaken until the components dissolved. Added to this mixture was 7.4 g of a 14 wt % polyvinyl butyral resin (BX-1, commercially obtained from Sekisui Chemical Co. Ltd., Japan) in tetrahydrofuran pre-mix solution, 0.44 g of maleic anhydride (Aldrich Chemical) in 2.0 g of tetrahydrofuran, and 0.83 g of a CGM mill-base containing 18.5 wt % of titanyl oxyphthalocyanine plus polyvinyl butyral resin at a ratio of 2.3:1 (BX-5, commercially obtained from Sekisui Chemical Co. Ltd., Japan) in tetrahydrofuran. The CGM mill-base was prepared as described for sample 1.

After mixing the solution on a mechanical shaker for about 1 hour, the single layer coating solution was coated onto an equivalent substrate as described for sample 1 using a knife coater with a 94 micron orifice followed by drying in an oven at 110° C. for 5 minutes.

Comparative Sample D

To form comparative sample D, a single layer organophotoreceptor coating solution was prepared by combining 1.59 g of MPCT-10 (a charge transfer material, commercially obtained from Mitsubishi Paper Mills, Tokyo, Japan), 2.29 g of a 20 wt % (4-n-butoxycarbonyl-9-fluorenylidene) malononitrile in tetrahydrofuran pre-mix solution, 4.0 g of tetrahydrofuran, 7.9 g of a 11.1 wt % polyvinyl butyral resin (BX-5, commercially obtained from Sekisui Chemical Co. Ltd., Japan) in tetrahydrofuran pre-mix solution, and 0.7 g of a CGM mill-base containing 18.7 wt % of titanyl oxyphthalocyanine plus polyvinyl butyral resin at a ratio of 2.3:1 (BX-5, commercially obtained from Sekisui Chemical Co. Ltd., Japan) in tetrahydrofuran. The CGM mill-base was prepared as described for sample 1.

After mixing the solution on a mechanical shaker for about 1 hour, 0.5 g of a 10 wt % triethylamine solution in tetrahydrofuran was added, the coating solution was briefly shaken, and then coated onto an equivalent substrate as described for sample 1 using a knife coater with a 94 micron orifice followed by drying in an oven at 85° C. for 15 minutes.

Comparative Sample E

To form comparative sample E, a single layer organophotoreceptor coating solution was prepared by combining 1.33 g of MPCT-10 (a charge transfer material, commercially obtained from Mitsubishi Paper Mills, Tokyo, Japan), 1.91 g of a 20 wt % (4-n-butoxycarbonyl-9-fluorenylidene) malononitrile in tetrahydrofuran pre-mix solution, 0.5 g of phthalic anhydride (Aldrich Chemical) in 5.5 g of tetrahydrofuran, 6.6 g of a 11.1 wt % polyvinyl butyral resin (BX-5, commercially obtained from Sekisui Chemical Co. Ltd., Japan) in tetrahydrofuran pre-mix solution, and 0.7 g of a CGM mill-base containing 18.7 wt % of titanyl oxyphthalocyanine plus polyvinyl butyral resin at a ratio of 2.3:1 (BX-5, commercially obtained from Sekisui Chemical Co. Ltd., Japan) in tetrahydrofuran. The CGM mill-base was prepared as described for sample 1.

After mixing the solution on a mechanical shaker for about 1 hour, 0.5 g of a 10 wt % triethylamine solution in tetrahydrofuran was added, the coating solution was briefly shaken, and then coated onto an equivalent substrate as described for sample 1 using a knife coater with a 94 micron orifice followed by drying in an oven at 85° C. for 15 minutes.

Example 4

Dry Electrostatic Testing and Properties of Organophotoreceptors

This example provides results of electrostatic testing on the organophotoreceptor samples formed as described in Example 3.

Electrostatic cycling performance of organophotoreceptors described herein with the epoxy modified hydrazone-based compounds was determined using in-house designed and developed test bed that can test, for example, up to three sample strips wrapped around a 160 mm diameter drum. The results on these samples are indicative of results that would be obtained with other support structures, such as belts, drums and the like, for supporting the organophotoreceptors.

For testing using a 160 mm diameter drum, three coated sample strips, each measuring 50 cm long by 8.8 cm wide, were fastened side-by-side and completely around an aluminum drum (50.3 cm circumference). In some embodiments, at least one of the strips is a control sample that is precision web coated and used as an internal reference point. A control sample with an inverted dual layer structure was used as an internal check of the tester. In this electrostatic cycling tester, the drum rotated at a rate of 8.13 cm /sec (3.2 ips), and the location of each station in the tester (distance and elapsed time per cycle) is given as shown in the following table:

TABLE 1

Electrostatic test stations around the 160 mm diameter drum at 8.13 cm/sec.

| Station | Degrees | Total Distance, cm | Total Time, sec |
|---|---|---|---|
| Front erase bar edge | 0° | Initial, 0 cm | Initial, 0 s |
| Erase Bar | 0–7.2° | 0–1.0 | 0–0.12 |
| Scorotron Charger | 113.1–135.3° | 15.8–18.9 | 1.94–2.33 |
| Laser Strike | 161.0° | 22.5 | 2.77 |
| Probe #1 | 181.1° | 25.3 | 3.11 |
| Probe #2 | 251.2° | 35.1 | 4.32 |
| Erase bar | 360° | 50.3 | 6.19 |

The erase bar is an array of laser emitting diodes (LED) with a wavelength of 720 nm that discharges the surface of the organophotoreceptor. The scorotron charger comprises a wire that permits the transfer of a desired amount of charge to the surface of the organophotoreceptor.

From the above table, the first electrostatic probe (Trek 344™ electrostatic meter, Trek, Inc. Medina, N.Y.) is located 0.34 s after the laser strike station and 0.78 s after the scorotron while the second probe (Trek™ 344 electrostatic meter) is located 1.21 s from the first probe and 1.99 s from the scorotron. All measurements are performed at ambient temperature and relative humidity.

Electrostatic measurements were obtained as a compilation of several runs on the test station. The first three diagnostic tests (prodtest initial, VlogE initial, dark decay initial) were designed to evaluate the electrostatic cycling of a new, fresh sample and the last three, identical diagnostic test (prodtest final, VlogE final, dark decay final) are run after cycling of the sample. In addition, measurements were made periodically during the test, as described under "longrun" below. The laser is operated at 780 nm wavelength, 600 dpi, 50 micron spot size, 60 nanoseconds/pixel expose time, 1,800 lines per second scan speed, and a 100% duty cycle. The duty cycle is the percent exposure of the pixel clock period, i.e., the laser is on for the full 60 nanoseconds per pixel at a 100% duty cycle.

Electrostatic Test Suite

1) PRODTEST: Charge acceptance ($V_{acc}$) and discharge voltage ($V_{dis}$) were established by subjecting the samples to corona charging (erase bar always on) for three complete drum revolutions (laser off); discharged with the laser @ 780 nm & 600 dpi on the forth revolution (50 um spot size, expose 60 nanoseconds/pixel, run at a scan speed of 1,800 lines per second, and use a 100% duty cycle); completely charged for the next three revolutions (laser off); discharged with only the erase lamp @ 720 nm on the eighth revolution (corona and laser off) to obtain residual voltage ($V_{res}$); and, finally, completely charged for the last three revolutions (laser off). The contrast voltage ($V_{con}$) is the difference between $V_{acc}$ and $V_{dis}$ and the functional dark decay ($V_{dd}$) is the difference in charge acceptance potential measured by probes #1 and #2.
2) VLOGE: This test measures the photoinduced discharge of the photoconductor to various laser intensity levels by monitoring the discharge voltage of the sample as a function of the laser power (exposure duration of 50 ns) with fixed exposure times and constant initial potentials. This test measures the photoinduced discharge of the photoconductor to various laser intensity levels by monitoring the discharge voltage of the sample as a function of the laser power (exposure duration of 50 ns) with fixed exposure times and constant initial potentials. The functional photosensitivity, $S_{780\ nm}$, and operational power settings was determined from this diagnostic test.

3) DARK DECAY: This test measures the loss of charge acceptance in the dark with time without laser or erase illumination for 90 seconds and can be used as an indicator of i) the injection of residual holes from the charge generation layer to the charge transport layer, ii) the thermal liberation of trapped charges, and iii) the injection of charge from the surface or aluminum ground plane.

4) LONGRUN: The sample was electrostatically cycled for 100 drum revolutions according to the following sequence per each sample-drum revolution. The sample was charged by the corona, the laser was cycled on and off (80–100° sections) to discharge a portion of the sample and, finally, the erase lamp discharged the whole sample in preparation for the next cycle. The laser was cycled so that the first section of the sample was never exposed, the second section was always exposed, the third section was never exposed, and the final section was always exposed. This pattern was repeated for a total of 100 drum revolutions, and the data was recorded periodically, after every 5th cycle for the 100 cycle longrun.

5) After the LONGRUN test, the PRODTEST, VLOGE, DARK DECAY diagnostic tests were run again.

The following Table shows the results from the initial and final prodtest diagnostic tests. The values for the charge acceptance voltage ($V_{acc}$, probe #1 average voltage obtained from the third cycle), discharge voltage ($V_{dis}$, probe #1 average voltage obtained from the fourth cycle) are reported for the initial and final cycles.

Example 5

Evaluation Ionization Potentials for Charge Transport Compounds

This example presents the evaluation of the ionization potentials for three samples and a comparative sample.

Samples for ionization potential (Ip) measurements was prepared by dissolving the compound in tetrahydrofuran. The solution was hand-coated on an aluminized polyester substrate that was precision coated with a methylcellulose-based adhesion sublayer to form a charge transport material (CTM) layer. The role of this sub-layer was to improve adhesion of the CTM layer, to retard crystallization of CTM, and to eliminate the electron photoemission from the Al layer through possible CTM layer defects. No photoemission was detected from the Al through the sub-layer at illumination with up to 6.4 eV quanta energy light. In addition, the adhesion sub-layer was conductive enough to avoid charge accumulation on it during measurement. The thickness of the sub-layer and CTM layer was each about 0.4 μm. No binder material was used with CTM in the preparation of the samples for Ip measurements. Three samples (16, 17 and 18) were prepared with compounds 2, 6, and 10, respectively.

The ionization potential was measured by an electron photoemission in air method similar to that described in "Ionization Potential of Organic Pigment Film by Atmospheric Photoelectron Emission Analysis," *Electrophotography,* 28, Nr. 4, p. 364 (1989) by E. Miyamoto, Y. Yamagu

TABLE 2

Dry Electrostatic Test Results Of Various Sample At The Beginning Of Cycling And After 100 Charge-Discharge Cycles.

| | Prodtest Initial | | | | | | Prodtest Final (100 cycles) | | | | |
|---|---|---|---|---|---|---|---|---|---|---|---|
| Sample ID # | $V_{acc}$ | $V_{dis}$ | $V_{Con}$ | $S_{780\ nm}$ | Dark Decay | $V_{Res}$ | $V_{acc}$ | $V_{dis}$ | $V_{Con}$ | Dark Decay | $V_{Res}$ |
| Sample 1 | 560 | 80 | 460 | 300 | 40 | 40 | 560 | 80 | 480 | 40 | 40 |
| Sample 2 | 430 | 130 | 300 | — | 60 | 40 | 430 | 190 | 240 | 50 | 40 |
| Sample 3 | 450 | 90 | 360 | — | 60 | 30 | 300 | 90 | 210 | 80 | 20 |
| Sample 4 | 559 | 74 | 485 | 251.5 | 52 | 32 | 571 | 71 | 500 | 46 | 29 |
| Sample 5 | 432 | 47 | 385 | 251.5 | 48 | 14 | 247 | 44 | 203 | 47 | 15 |
| Sample 6 | 550 | 140 | 410 | 180 | 40 | 60 | 560 | 160 | 400 | 40 | 70 |
| Sample 7 | 450 | 170 | 280 | — | 45 | 80 | 440 | 170 | 270 | 60 | 90 |
| Sample 8 | 470 | 240 | 230 | — | 50 | 90 | 440 | 230 | 210 | 60 | 100 |
| Sample 9 | 570 | 175 | 395 | — | 50 | 60 | 590 | 185 | 405 | 50 | 60 |
| Sample 10 | 465 | 180 | 285 | — | 50 | 70 | 420 | 175 | 250 | 50 | 70 |
| Sample 11 | 500 | 160 | 340 | 125 | 60 | 40 | 470 | 150 | 320 | 60 | 50 |
| Sample 12 | 380 | 200 | 180 | — | 60 | 80 | 320 | 200 | 120 | 80 | 70 |
| Sample 13 | 370 | 180 | 190 | — | 80 | 40 | 280 | 160 | 120 | 60 | 40 |
| Sample 14 | 545 | 340 | 205 | — | 65 | 110 | 560 | 355 | 205 | 70 | 130 |
| Sample 15 | 380 | 201 | 180 | — | 75 | 50 | 330 | 190 | 140 | 80 | 50 |
| Comparative Sample A | 650 | 50 | 600 | 340 | 40 | 20 | 670 | 100 | 570 | 40 | 20 |
| Comparative Sample B | 500 | 50 | 450 | 310 | 40 | 15 | 320 | 60 | 260 | 40 | 15 |
| Comparative Sample C | 320 | 40 | 280 | — | 60 | 20 | 140 | 50 | 90 | 20 | 20 |
| Comparative Sample D | 614 | 35 | 580 | 376 | 45 | 10 | 581 | 34 | 550 | 46 | 10 |
| Comparative Sample E | 459 | 31 | 428 | 470 | 49 | 11 | 171 | 30 | 141 | 55 | 14 |

In the above table, the radiation sensitivity (Sensitivity at 780 nm in $m^2/J$) of the xerographic process was determined from the information obtained during the VLOGE diagnositc run by calculating the reciprocal of the product of the laser power required to discharge the photoreceptor to ½ of its initial potential, the exposure duration, and 1/spot size.

chi, and M. Yokoyama, which is hereby incorporated by reference. Each sample was illuminated with monochromatic light from the quartz monochromator with a deuterium lamp source. The power of the incident light beam was $2–5·10^{-8}$ W. The negative voltage of −300 V was supplied to the sample substrate. The counter-electrode with the 4.5—15 $mm^2$ slit for illumination was placed at 8 mm distance from the sample surface. The counter-electrode was connected to the input of the BK2-16 type electrometer, working in the open impute regime, for the photocurrent measurement. A $10^{-15}$–$10^{-12}$ amp photocurrent was flowing in the circuit under illumination. The photocurrent, I, was strongly dependent on the incident light photon energy hν. The $I^{0.5}$=f(hν) dependence was plotted. Usually the dependence of the square root of photocurrent on incident light quanta energy is well described by linear relationship near the threshold [see references "Ionization Potential of Organic Pigment Film by Atmospheric Photoelectron Emission Analysis," *Electrophotography,* 28, Nr. 4, p. 364 (1989) by E. Miyamoto, Y. Yamaguchi, and M. Yokoyama; and "Photoemission in Solids," Topics in Applied Physics, 26, 1–103 (1978) by M. Cordona and L. Ley, both of which are incorporated herein by reference]. The linear part of this dependence was extrapolated to the hvaxis and Ip value was determined as the photon energy at the interception point. The ionization potential measurement has an error of ±0.03 eV. The ionization potential data are listed in Table 3.

TABLE 3

Ionization Potential and Mobility Values.

| Sample | α $(cm/V)^{0.5}$ | Mobility $(cm^2/Vs)$ | $I_p$ (eV) |
|---|---|---|---|
| Sample 16 | — | — | 5.47 |
| Sample 17 | — | — | 5.43 |
| Sample 18 | — | — | 5.37 |
| Sample 19 | 0.0039 | $1.7 \cdot 10^{-6}$ | — |
| Sample 20 | 0.0050 | $1.0 \cdot 10^{-5}$ | — |
| Sample 21 | 0.0055 | $4.8 \cdot 10^{-7}$ | — |
| Sample 22 | 0.0059 | $3.8 \cdot 10^{-6}$ | — |
| Sample 23 | 0.0057 | $1.5 \cdot 10^{-5}$ | — |

Example 6

This example describes measurements of hole mobility for organophotoreceptor samples.

The hole drift mobility was measured by a time of flight technique as described in "The discharge kinetics of negatively charged Se electrophotographic layers," Lithuanian Journal of Physics, 6, p. 569–576 (1966) by E. Montrimas, V. Gaidelis, and A. Pažėra, which is hereby incorporated by reference. Positive corona charging created an electric field inside the CTM layer. The charge carriers were generated at the layer surface by illumination with pulses of nitrogen laser (pulse duration was 2 ns, wavelength 337 nm). The layer surface potential decreased as a result of pulse illumination was up to 1–5% of initial potential before illumination. The capacitance probe that was connected to the wide frequency band electrometer measured the speed of the surface potential dU/dt. The transit time $t_t$ was determined by the change (kink) in the curve of the dU/dt transient in linear or double logarithmic scale. The drift mobility was calculated by the formula $\mu=d^2/U_0 \cdot t_t$, where d is the layer thickness and $U_0$ is the surface potential at the moment of illumination. Mobility values were evaluated at electric field strength, E, of $6.4·10^5$ V/cm. The mobility field dependencies may be approximated by the function $$\mu \sim e^{\alpha\sqrt{E}}$$

where α is parameter characterizing mobility field dependence.

Five samples as follows were prepared from the three charge transport compounds described above in Example 1.

Sample 19

A mixture of 0.1 g of compound 2 and 0.1 g of polyvinylbutyral (PVB1, Aldrich cat. # 41,843-9, commercially obtained from Aldrich, Milwaukee, Wis.) was dissolved in 2 ml of THF. The solution was coated on the polyester film with conductive Al layer by the dip roller method. After drying for 1 hour at 80° C., a clear 10 μm thick layer was formed. The hole mobility of sample 19 was measured, the results are presented in Table 3 above.

Sample 20

Sample 20 was prepared according the procedure for sample 19, except that polyvinylbutyral S-LEC B BX-1 (commercially obtained from Sekisui Chemical Co. Ltd., Japan) was used in place of PVB1. The mobility measurement results are in Table 3.

Sample 21

Sample 21 was prepared according to the procedure for sample 19 except that compound 6 was used in place of compound 2. The mobility measurement results are in Table 3.

Sample 22

Sample 22 was prepared according to the procedure for sample 20 except that compound 9 was used in place of compound 2. The mobility measurement results are in Table 3.

Sample 23

Sample 23 was prepared according to the procedure for sample 22 except that polycarbonate Iupilon® Z-200 (commercially obtained from Mitsubishi Gas Chemical) was used in place of polyvinyl butyral. The mobility measurement results are in Table 3.

As understood by those skilled in the art, additional substitution, variation among substituents, and alternative methods of synthesis and use may be practiced within the scope and intent of the present disclosure of the invention. The embodiments above are intended to be illustrative and not limiting. Additional embodiments are within the claims. Although the present invention has been described with reference to particular embodiments, workers skilled in the art will recognize that changes may be made in form and detail without departing from the spirit and scope of the invention.

What is claimed is:

1. An organophotoreceptor comprising an electrically conductive substrate and a photoconductive element on the electrically conductive substrate, the photoconductive element comprising:

(a) a charge transport compound having the formula

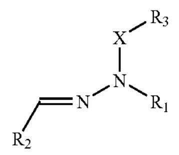

where X is a divalent hydrocarbon group of 1 to 30 carbon atoms, or a divalent hydrocarbon group of 1 to 30 carbon atoms where there is at least one substitution of a carbon atom by a heteroatom provided that no two heteroatoms may be adjacent within the backbone of an aliphatic divalent hydrocarbon group, $R_1$ is an aromatic group or a heterocyclic group, $R_2$ is a (N,N-disubstituted)arylamine group, and $R_3$ is an epoxy group; and (b) a charge generating compound.

2. An organophotoreceptor according to claim 1 wherein the photoconductive element further comprises an electron transport compound.

3. An organophotoreceptor according to claim 1 wherein the charge transport compound has the formula

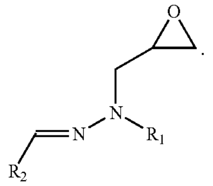

4. An organophotoreceptor according to claim 1 wherein the photoconductive element further comprises a polymer binder.

5. An organophotoreceptor according to claim 4 wherein the polymer binder comprises a reactive functionality selected from the group consisting of hydroxyl group, carboxyl group, amino group, thiol group and reaction products of these functional groups with an epoxy functional group or an acid anhydride.

6. An organophotoreceptor according to claim 5 wherein the at least a photoconductive layer further comprises a cyclic acid anhydride or the reaction product of a cyclic acid anhydride and the epoxy functional group and the polymer reactive functionality.

7. An organophotoreceptor according to claim 1 wherein the epoxy group is an epoxy linkage to a functional group of a polymer binder.

8. An organophotoreceptor according to claim 7 wherein a crosslinking agent is bonded between the epoxy linkage and the polymer binder.

9. An organophotoreceptor according to claim 1 wherein the (N,N-disubstituted)arylamine group is a p-(N,N-disubstituted)arylamine group.

10. An organophotoreceptor according to claim 1 wherein the (N,N-disubstituted)arylamine group comprises a triphenyl amine group, a carbazole group or a julolidine group.

11. An organophotoreceptor according to claim 1 wherein the $R_1$ group is a phenyl group.

12. An electrophotographic imaging apparatus comprising:

(a) a light imaging component; and (b) an organophotoreceptor oriented to receive light from the light imaging component, the organophotoreceptor comprising an electrically conductive substrate and a photoconductive element on the electrically conductive substrate, the photoconductive element comprising:

(i) a charge transport compound having the formula

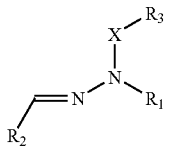

where X is a divalent hydrocarbon group of 1 to 30 carbon atoms, or a divalent hydrocarbon group of 1 to 30 carbon atoms where there is at least one substitution of a carbon atom by a heteroatom provided that no two heteroatoms may be adjacent within the backbone of an aliphatic divalent hydrocarbon group, $R_1$ is an aryl group or a heterocyclic group, $R_2$ is a (N,N-disubstituted)arylamine group, and $R_3$ is an epoxy group; and (ii) a charge generating compound.

13. An electrophotographic imaging apparatus according to claim 12 wherein the charge transport compound has the formula

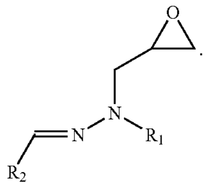

14. An electrophotographic imaging apparatus according to claim 12 wherein the photoconductive element further comprises an electron transport compound.

15. An electrophotographic imaging apparatus according to claim 12 wherein the photoconductive element further comprises a binder.

16. An electrophotographic imaging apparatus according to claim 12 wherein the binder comprises a reactive functionality selected from the group consisting of a hydroxyl group, a carboxyl group, an amino group, a thiol group and the reaction products of these functional groups with an epoxy group or a crosslinking agent bonded to an epoxy group.

17. An electrophoto graphic imaging apparatus according to claim 16 wherein the photoconductive element further comprises a crosslinking agent or the reaction product of the crosslinking agent with the epoxy functional group and the polymer reactive functionality.

18. An electrophotographic imaging apparatus according to claim 12 wherein the (N,N-disubstituted)arylamine group comprises a triphenyl amine group, a carbazole group or a julolidine group.

* * * * *